United States Patent
Zhao

(10) Patent No.: US 12,380,533 B2
(45) Date of Patent: Aug. 5, 2025

(54) EFFICIENT IMAGE DEMOSAICING AND LOCAL CONTRAST ENHANCEMENT

(71) Applicant: Intuitive Surgical Operations, Inc., Sunnyvale, CA (US)

(72) Inventor: Wenyi Zhao, Weston, FL (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 0 days.

(21) Appl. No.: 18/376,987

(22) Filed: Oct. 5, 2023

(65) Prior Publication Data
US 2024/0029199 A1    Jan. 25, 2024

Related U.S. Application Data

(63) Continuation of application No. 17/740,121, filed on May 9, 2022, now Pat. No. 11,816,811, which is a
(Continued)

(51) Int. Cl.
| | |
|---|---|
| *G06T 5/00* | (2024.01) |
| *G06T 3/4015* | (2024.01) |
| *G06T 5/20* | (2006.01) |
| *H04N 9/82* | (2006.01) |
| *H04N 23/84* | (2023.01) |
| *H04N 25/13* | (2023.01) |
| *H04N 23/50* | (2023.01) |

(52) U.S. Cl.
CPC ......... *G06T 3/4015* (2013.01); *H04N 23/843* (2023.01); *H04N 25/134* (2023.01); *A61B 2576/00* (2013.01); *H04N 23/555* (2023.01)

(58) Field of Classification Search
CPC .............. G06T 3/4015; H04N 9/04557; H04N 9/04515; H04N 2005/2255; A61B 2576/00
USPC ....................................................... 348/167
See application file for complete search history.

(56) References Cited

U.S. PATENT DOCUMENTS

| | | |
|---|---|---|
| 3,971,065 A | 7/1976 | Bayer |
| 4,642,678 A | 2/1987 | Cok |
| (Continued) | | |

OTHER PUBLICATIONS

Alleysson, David et al., "Linear Demosaicing Inspired by the Human Visual System," IEEE Transactions on Image Processing, vol. 14, No. 4, Apr. 2005, pp. 1-12.
(Continued)

*Primary Examiner* — Albert Kir

(57) ABSTRACT

An exemplary method includes receiving a frame of raw pixels captured by an image capture sensor, a particular location in the frame of raw pixels including a captured color pixel value of a first color component of a first color space; generating, for the particular location in the frame of raw pixels, a vertical color difference signal and a horizontal color difference signal using information from the frame of raw pixels; determining that the particular location is missing a color pixel value of a second color component of the first color space; generating a reconstructed color pixel value of the second color component based on the vertical color difference signal and the horizontal color difference signal; and transforming the vertical color difference signal and the horizontal color difference signal into chrominance pixel values in a second color space that is different from the first color space.

17 Claims, 17 Drawing Sheets

Related U.S. Application Data continuation of application No. 16/917,483, filed on Jun. 30, 2020, now abandoned, which is a continuation of application No. 16/239,489, filed on Jan. 3, 2019, now Pat. No. 10,733,703, which is a continuation of application No. 14/451,621, filed on Aug. 5, 2014, now Pat. No. 10,210,599.

(60) Provisional application No. 61/864,090, filed on Aug. 9, 2013.

(56) References Cited

U.S. PATENT DOCUMENTS

| | | | |
|---|---|---|---|
| 5,563,661 A | 10/1996 | Takahashi et al. | |
| 5,629,734 A | 5/1997 | Hamilton, Jr. et al. | |
| 5,864,342 A * | 1/1999 | Kajiya | G06T 11/001 345/589 |
| 6,642,962 B1 * | 11/2003 | Lin | G06T 3/4007 348/252 |
| 8,199,216 B2 | 6/2012 | Hwang | |
| 8,340,407 B2 | 12/2012 | Kalman | |
| 9,516,239 B2 * | 12/2016 | Blanquart | H04N 25/75 |
| 9,898,831 B2 * | 2/2018 | Thivin | H04N 1/60 |
| 10,210,599 B2 | 2/2019 | Zhao et al. | |
| 10,470,720 B2 | 11/2019 | Li et al. | |
| 10,733,703 B2 | 8/2020 | Zhao | |
| 2003/0169353 A1 | 9/2003 | Keshet et al. | |
| 2005/0200733 A1 | 9/2005 | Malvar et al. | |
| 2006/0279585 A1 | 12/2006 | Milanfar et al. | |
| 2009/0010539 A1 | 1/2009 | Guarnera et al. | |
| 2009/0174811 A1 * | 7/2009 | Sung | H04N 19/428 348/E11.006 |
| 2009/0252411 A1 | 10/2009 | Siddiqui et al. | |
| 2010/0053351 A1 * | 3/2010 | Lukac | H04N 25/134 348/222.1 |
| 2010/0208989 A1 * | 8/2010 | Narroschke | H04N 19/186 382/233 |
| 2011/0211752 A1 | 9/2011 | Grafulla-Gonzalez | |
| 2012/0209287 A1 | 8/2012 | Zhao et al. | |
| 2013/0300846 A1 | 11/2013 | Miller et al. | |
| 2015/0042775 A1 * | 2/2015 | Zhao | H04N 25/134 348/71 |
| 2017/0118477 A1 * | 4/2017 | Suzuki | G06T 3/4015 |
| 2020/0334786 A1 | 10/2020 | Zhao | |
| 2022/0261956 A1 | 8/2022 | Zhao | |
| 2024/0107181 A1 * | 3/2024 | Kim | H04N 23/84 |

OTHER PUBLICATIONS

Chang L., et al., "Hybrid Color Filter Array Demosaicking for Effective Artifact Suppression," Journal of Electronic Imaging, 2006, vol. 15 (1), 013003, pp. 1-40.

Vertut, J., and Coiffet, P., "Robot Technology: Teleoperation and Robotics Evolution and Development," English translation, Prentice-Hall, Inc., Inglewood Cliffs, NJ, USA 1986, vol. 3A, 332 pages.

Zhang, Lei and Xiaolin Wu, "Color Demosaicking via Directional Linear Minimum Mean Square-Error Estimation," IEEE Transactions on Image Processing, vol. 14, No. 12, Dec. 2005, pates 2167-2178.

\* cited by examiner

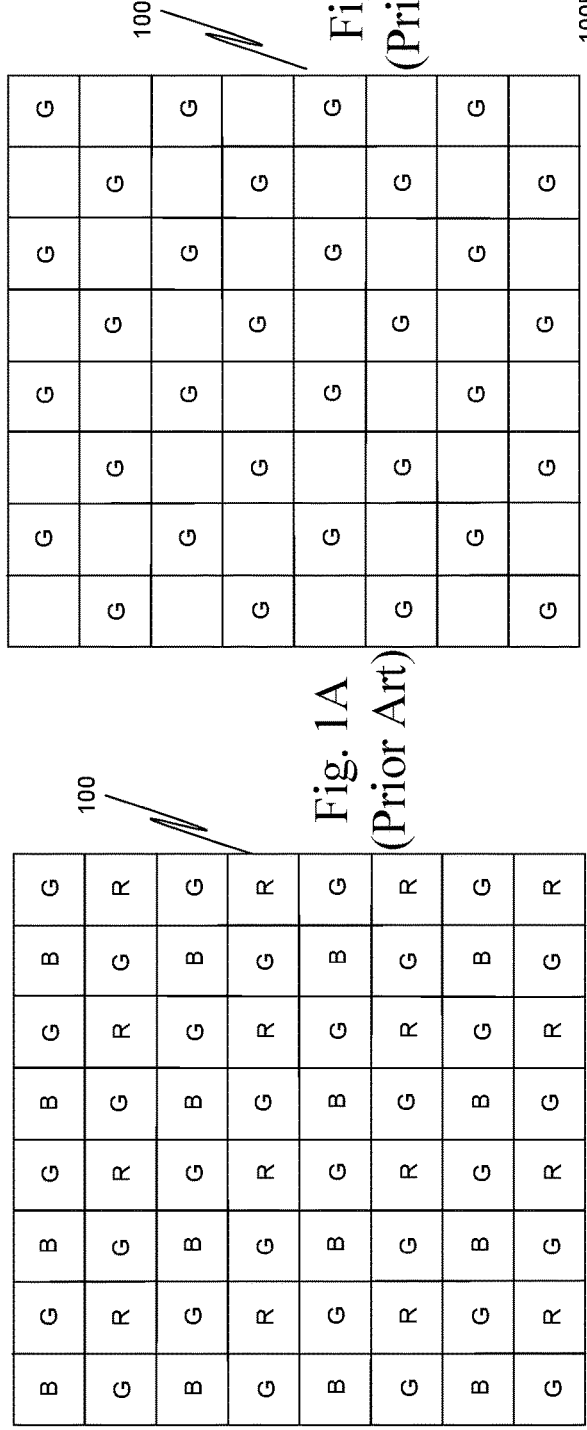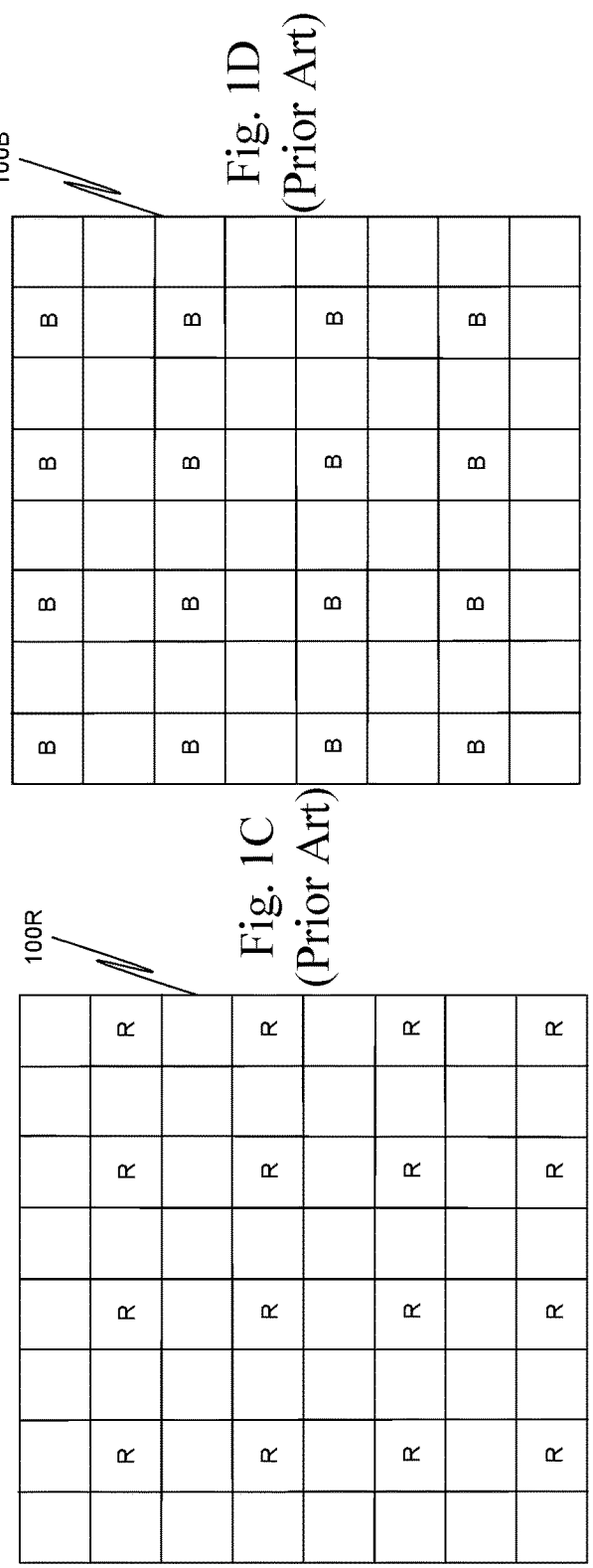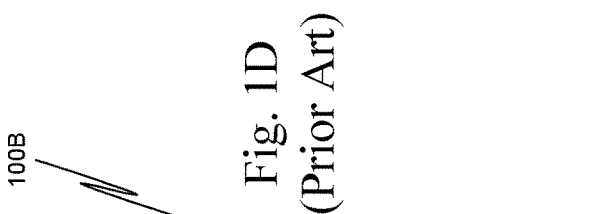

| r, g, B | r, G, b | r, g, B | r, G, b | r, g, B | r, G, b | r, g, B | r, G, b |
|---|---|---|---|---|---|---|---|
| r, G, b | R, g, b | r, G, b | R, g, b | r, G, b | R, g, b | r, G, b | R, g, b |
| r, g, B | r, G, b | r, g, B | r, G, b | r, g, B | r, G, b | r, g, B | r, G, b |
| r, G, b | R, g, b | r, G, b | R, g, b | r, G, b | R, g, b | r, G, b | R, g, b |
| r, g, B | r, G, b | r, g, B | r, G, b | r, g, B | r, G, b | r, g, B | r, G, b |
| r, G, b | R, g, b | r, G, b | R, g, b | r, G, b | R, g, b | r, G, b | R, g, b |
| r, g, B | r, G, b | r, g, B | r, G, b | r, g, B | r, G, b | r, g, B | r, G, b |
| r, G, b | R, g, b | r, G, b | R, g, b | r, G, b | R, g, b | r, G, b | R, g, b |

| GBdiff_h = g_h - B GBdiff_v= g_v - B | GBdiff_h = G - b_h GRdiff_v =G - r_v | GBdiff_h = g_h - B GBdiff_v= g_v - B | GBdiff_h = G - b_h GRdiff_v =G - r_v | GBdiff_h = g_h - B GBdiff_v= g_v - B |
|---|---|---|---|---|
| GRdiff_h = G - r_h GBdiff_v = G - b_v | GRdiff_h = g_h - R GRdiff_v= g_v - R | GRdiff_h = G - r_h GBdiff_v = G - b_v | GRdiff_h = g_h - R GRdiff_v= g_v - R | GRdiff_h = G - r_h GBdiff_v = G - b_v |
| GBdiff_h = g_h - B GBdiff_v= g_v - B | GBdiff_h = G - b_h GRdiff_v =G - r_v | GBdiff_h = g_h - B GBdiff_v= g_v - B | GBdiff_h = G - b_h GRdiff_v =G - r_v | GBdiff_h = g_h - B GBdiff_v= g_v - B |
| GRdiff_h = G - r_h GBdiff_v = G - b_v | GRdiff_h = g_h - R GRdiff_v= g_v - R | GRdiff_h = G - r_h GBdiff_v = G - b_v | GRdiff_h = g_h - R GRdiff_v= g_v - R | GRdiff_h = G - r_h GBdiff_v = G - b_v |
| GBdiff_h = g_h - B GBdiff_v= g_v - B | GBdiff_h = G - b_h GRdiff_v =G - r_v | GBdiff_h = g_h - B GBdiff_v= g_v - B | GBdiff_h = G - b_h GRdiff_v =G - r_v | GBdiff_h = g_h - B GBdiff_v= g_v - B |

Fig. 5C

| , g, B (x-1, y+1) | , G, | , g, B (x+1, y+1) |
|---|---|---|
| , G, | R, g, (x, y) | , G, |
| , g, B (x-1, y-1) | , G, | , g, B (x+1, y-1) |

Fig. 11A

| R, g, (x-1, y+1) | , G, | R, g, (x+1, y+1) |
|---|---|---|
| , G, | , g, B (x, y) | , G, |
| R, g, (x-1, y-1) | , G, | R, g, (x+1, y-1) |

Fig. 11B

| , G, (x-1, y+1) | R, g, b (x, y+1) | , G, (x+1, y+1) |
|---|---|---|
| r, g, B (x-1, y) | , G, (x, y) | r, g, B (x+1, y) |
| , G, (x-1, y-1) | R, g, b (x, y-1) | , G, (x+1, y-1) |

Fig. 11C

| , G, (x-1, y+1) | r, g, B (x, y+1) | , G, (x+1, y+1) |
|---|---|---|
| R, g, b (x-1, y) | , G, (x, y) | R, g, b (x+1, y) |
| , G, (x-1, y-1) | r, g, B (x, y-1) | , G, (x+1, y-1) |

Fig. 11D

| | | (x, y+2) G | | |
|---|---|---|---|---|
| | | (x, y+1) R | | |
| (x-2, y) G | (x-1, y) B | (x, y) G | (x+1, y) B | (x+2, y) G |
| | | (x, y-1) R | | |
| | | (x, y-2) G | | |

Fig. 12A

| | | (x, y+2) G | | |
|---|---|---|---|---|
| | | (x, y+1) B | | |
| (x-2, y) G | (x-1, y) R | (x, y) G | (x+1, y) R | (x+2, y) G |
| | | (x, y-1) B | | |
| | | (x, y-2) G | | |

Fig. 12B

| | | (x, y+2) R | | |
|---|---|---|---|---|
| | | (x, y+1) G | | |
| (x-2, y) R | (x-1, y) G | (x, y) R | (x+1, y) G | (x+2, y) R |
| | | (x, y-1) G | | |
| | | (x, y-2) R | | |

Fig. 12C

| | | (x, y+2) B | | |
|---|---|---|---|---|
| | | (x, y+1) G | | |
| (x-2, y) B | (x-1, y) G | (x, y) B | (x+1, y) G | (x+2, y) B |
| | | (x, y-1) G | | |
| | | (x, y-2) B | | |

Fig. 12D

| , g, B (x-1, y+1) | , G, G.Bdiff_h G.Rdiff_v (x, y+1) | , g, B (x+1, y+1) |
|---|---|---|
| , G, G.Rdiff_h G.Bdiff_v (x-1, y) | R, g, G.Rdiff_h G.Rdiff_v (x, y) | , G, G.Rdiff_h G.Bdiff_v (x+1, y) |
| , g, B (x-1, y-1) | , G, G.Bdiff_h G.Rdiff_v (x, y-1) | , g, B (x+1, y-1) |

Fig. 15A

| R, g, (x-1. y+1) | , G, G.Rdiff_h G.Bdiff_v (x, y+1) | R, g, (x+1. y+1) |
|---|---|---|
| , G, G.Bdiff_h G.Rdiff_v (x-1, y) | , g, B G.Bdiff_h G.Bdiff_v (x. y) | , G, G.Bdiff_h G.Rdiff_v (x+1, y) |
| R, g, (x-1. y-1) | , G, G.Rdiff_h G.Bdiff_v (x, y-1) | R, g, (x+1. y-1) |

Fig. 15B

| , G, G.Rdiff_h G.Bdiff_v (x-1, y+1) | R, g, (x, y+1) | , G, G.Rdiff_h G.Bdiff_v (x+1, y+1) |
|---|---|---|
| , g, B (x-1, y) | , G, G.Bdiff_h G.Rdiff_v (x, y) | , g, B (x+1, y) |
| , G, G.Rdiff_h G.Bdiff_v (x-1, y-1) | R, g, (x, y-1) | , G, G.Rdiff_h G.Bdiff_v (x+1, y-1) |

Fig. 15C

| , G, G.Bdiff_h G.Rdiff_v (x-1, y+1) | , g, B (x, y+1) | , G, G.Bdiff_h G.Rdiff_v (x+1, y+1) |
|---|---|---|
| R, g, (x-1, y) | , G, (x, y) | R, g, (x+1, y) |
| , G, G.Bdiff_h G.Rdiff_v (x-1, y-1) | , g, B (x, y-1) | , G, G.Bdiff_h G.Rdiff_v (x+1, y-1) |

Fig. 15D

EFFICIENT IMAGE DEMOSAICING AND LOCAL CONTRAST ENHANCEMENT

RELATED APPLICATIONS

This application is a continuation of U.S. patent application Ser. No. 17/740,121 filed May 9, 2022, which is a continuation of U.S. patent application Ser. No. 16/917,483 filed Jun. 30, 2020, which is a continuation of U.S. patent application Ser. No. 16/239,489 filed Jan. 3, 2019 and issued as U.S. Pat. No. 10,733,703, which application is a continuation of U.S. patent application Ser. No. 14/451,621 filed Aug. 5, 2014 and issued as U.S. Pat. No. 10,210,599, which claims priority to and the benefit of U.S. Provisional Application No. 61/864,090 filed Aug. 9, 2013, each of which is incorporated herein by reference in its entirety.

BACKGROUND

Field of Invention

Aspects of this invention are related to color imaging in surgical systems, and are more particularly related to demosaicing a frame of pixels.

Related Art

Many color cameras capture images using a single sensor array. The camera includes a color filter array and an image capture sensor. The color filter array filters the incoming light so that each pixel of the image capture sensor receives only one of the primary colors. Spatial resolution is sacrificed in view of the compact size of the single sensor array and the ability to generate full resolution images from the captured pixels.

A commonly used color filter array is referred to as a Bayer pattern color filter array. The Bayer pattern color filter array is described, for example, in U.S. Pat. No. 3,971,065, which is incorporated herein by reference.

FIG. 1A is a representation of part of a Bayer pattern color filter array. The Bayer pattern color filter array has a mosaic pattern. Each pixel in the Bayer pattern color filter array passes primarily a single primary color in a color space. In a color space with red, green, and blue color components, the pixels in the array selectively pass green light, red light, and blue light to the image capture sensor. Typically, the Bayer pattern color filter array is a mosaic with one-quarter of the total number of pixels being red (R) filters, one-half of the total number of pixels being green (G) filters; and one-quarter of the total number of pixels being blue (B) filters.

In the image acquired by the image capture sensor, no color component has the full resolution of the image capture sensor, i.e., the total number of pixels captured by the image capture sensor. As shown in FIG. 1$i$, the captured green pixels G are only one-half of the total number of pixels captured by the image capture sensor. In FIGS. 1C and 1D, the captured red pixels and blue pixels are each only one-quarter of the total number of pixels captured by the image capture sensor. To obtain a complete full resolution set of pixels for each of the color components, a process called demosaicing is commonly used. Demosaicing is a process used to reconstruct a full color image from the color samples that are output from an image capture sensor overlaid with a color filter array.

Since humans are sensitive to edge structures in an image, many adaptive demosaicing methods try to avoid interpolating across edges. Some examples of these methods are presented in U.S. Pat. No. 5,629,734 (disclosing "Adaptive Color Plane Interpolation in Single Sensor Color Electronic Camera") and L. Zhang and X. Wu, "Color Demosaicing The Directional Linear Minimum Mean Square Error Estimation," IEEE Trans. on Imaging Processing, 2005.

U.S. Pat. No. 5,629,734 describes an adaptive interpolation demosaicing process that utilizes a second order Laplacian filter. The filter uses the absolute value of a second order blue-red color gradient plus the absolute value of a first order green color difference to select an edge direction in the adaptive interpolation demosaicing process.

Each demosaicing process tries to improve on one or more of the factors that are important to demosaicing. A few factors considered in selecting a demosaicing process include: 1) reconstruction quality in terms of edges, 2) reconstruction quality in terms of color artifacts, 3) process complexity, and 4) reconstruction quality under noise. Unfortunately, many of the demosaicing processes that perform well with respect to the first, second, and fourth factors are complex, and it is challenging to implement them, without expensive hardware, in a surgical system that requires a real-time video display.

SUMMARY

In one aspect, an efficient demosaicing process receives a frame of pixels. The frame of pixels was captured in an image capture unit including a red-green-blue Bayer color filter array. The efficient demosaicing process generates a plurality of color difference signals from pixels in the frame and then filters each of the color difference signals in the plurality of color difference signals. The efficient demosaicing process constructs a full resolution frame of green pixels by adaptively generating missing green pixels from the filtered color difference signals. The adaptive generation process includes selecting the filtered color difference signal used with a local edge estimator that is specific to each pixel and so different pixels can have different local edge estimators.

In one aspect, the generation of the plurality of color difference signals includes generating a series expansion of each missing pixel at each location in the frame. The series expansion is an estimated value of the missing pixel and so an estimated pixel is generated. In one aspect, the series expansion is used to generate an estimated horizontal pixel and an estimated vertical pixel.

The generation of a plurality of color difference signals includes generating, for one of a red pixel and a blue pixel, a difference of an estimated green pixel and the one of the red pixel and the blue pixel. The generation of a plurality of color difference signals also includes generating, for a green pixel, a difference of the value of the green pixel and one of an estimated red pixel and an estimated blue pixel.

In another aspect, the efficient demosaicing process is enhanced by including local contrast enhancement. In this method, a frame of pixels is received. The efficient demosaicing process with local contrast enhancement generates a plurality of color difference signals from pixels in the frame, and then filters each of the color difference signals in the plurality of color difference signals. The efficient demosaicing process constructs a full resolution frame of green pixels by adaptively generating missing green pixels from the filtered color difference signals. The adaptive generation process includes selecting the filtered color difference signal used in the generating with a local edge estimator that is specific to each pixel and so different pixels can have different local edge estimators.

The efficient demosaicing process with local contrast enhancement transforms a green pixel in the full resolution frame of green pixels into a brightness pixel by scaling the green pixel with a scale factor. The brightness pixel is in a color space different from the red-green-blue color space. The efficient demosaicing process with local contrast enhancement also transforms the plurality of filtered color difference signals into chrominance pixels in the color space different from a red-green-blue color space.

BRIEF DESCRIPTION OF THE DRAWINGS

FIGS. 1A to 1D are different illustrations of the mosaic pixel layout in frame of pixels captured in an image capture unit with a single image capture sensor and a red-green-blue color filter array.

FIG. 4 illustrates a portion of a full resolution frame of pixels created by the process of FIG. 3, in one aspect.

FIG. 5C illustrates the color difference signals generated at each location in the block of FIG. 5A.

FIGS. 11A to 11D are representations of information used in reconstruct red and blue pixels process of FIG. 3.

FIGS. 12A to 12D show the pixel color layout and coordinate position used in the series expansion to generate the estimated pixel values.

FIGS. 15A to 15D are representations of information used in generating the color difference signals in the process of FIG. 14.

Figure 2:
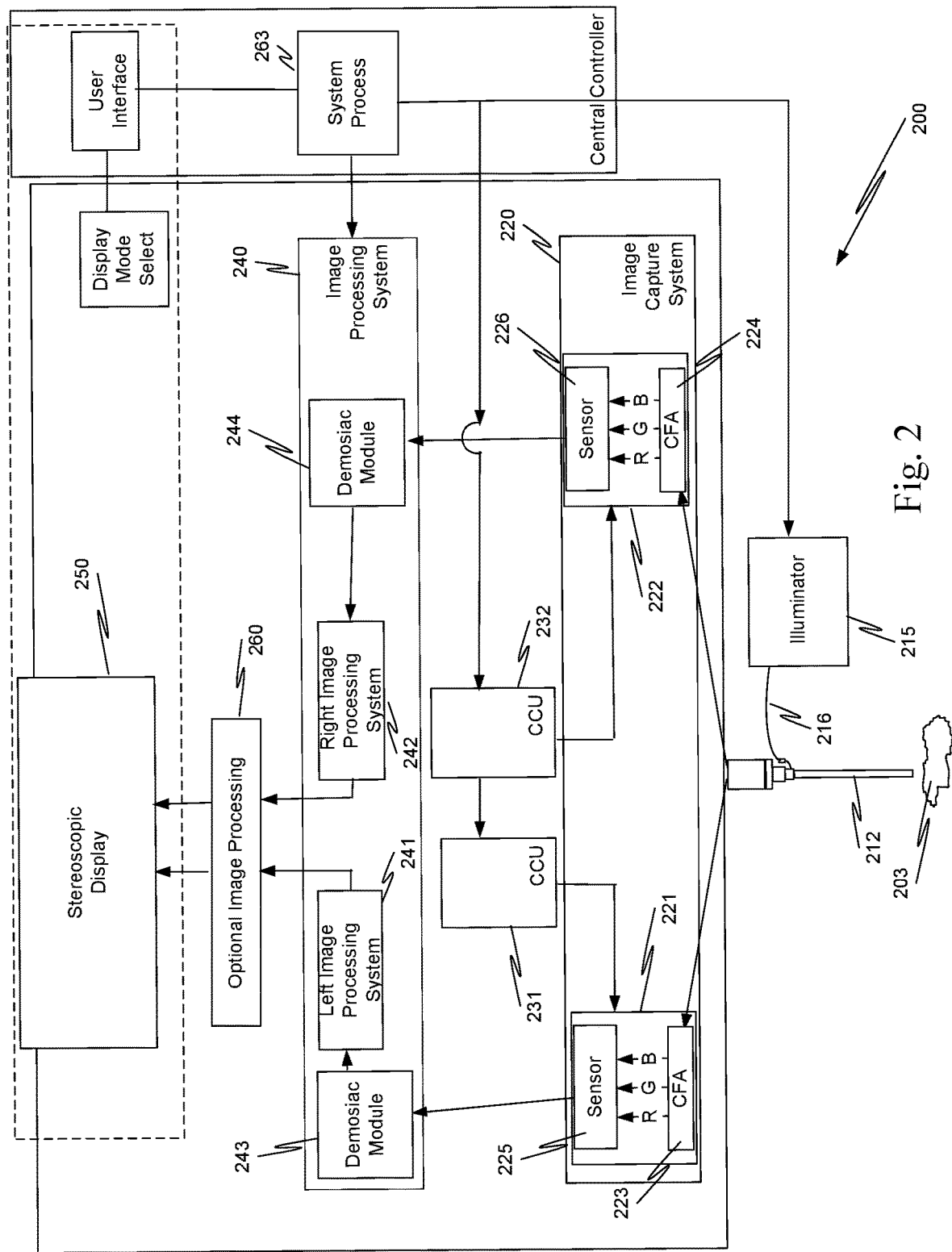
FIG. 2 is schematic diagram of a teleoperated surgical system including an imaging processing system that includes demosaicing modules that perform an efficient demosaicing process that in one aspect includes local contrast enhancement.

In the drawings, for single digit figure numbers, the first digit of a reference number indicates the figure number in which an element with that reference number first appeared. For double-digit figure numbers, the first two digits of a reference number indicate the figure number in which an element with that reference number first appeared.

DETAILED DESCRIPTION

Aspects of this invention are used in a surgical system, e.g., the da Vinci® Surgical Robotic System commercialized by Intuitive Surgical, Inc. of Sunnyvale, California, when color imaging is used (da Vinci® is a registered trademark of Intuitive Surgical, Inc. of Sunnyvale, California.). An efficient demosaicing process turns raw scenes from a single-chip CFA (color filter array) sensor to color scenes that make up a video sequence in the surgical system. In one aspect, the efficient demosaicing process is combined with local contrast enhancement in an efficient way that is particularly effective for surgical scenes.

The efficient demosaicing process has good reconstruction quality in terms of edges, good reconstruction quality in terms of color artifacts, and good reconstruction quality under noise. In one aspect, the efficient demosaicing process is implemented in hardware so that the delay in the image processing introduced by the demosaicing process is reduced significantly in comparison to prior art software based methods.

As in any demosaicing process, the efficient demosaicing process generates full resolution sets of red, green, and blue pixels from the partial sets of red, green, and blue pixels captured by the image capture sensor. The image capture sensor captures a monochromatic image. However, since the locations in the image capture sensor that correspond to the red, green, and blue pixels are known, each captured pixel is assigned the appropriate color and processed as a pixel of that color.

An example of the efficient demosaicing process is presented for an image capture unit that includes a Bayer pattern color filter array and an image capture sensor. It is known that the Bayer pattern color filter array has the best spatial arrangement for a three-color color filter array. See, for example, U.S. Pat. No. 3,971,056 (disclosing "Color Imaging Array"). The demosaicing process relies upon well-known assumptions that the different red, green, and blue color components are correlated. See U.S. Pat. No. 4,642,678 (disclosing "Signal Processing Method and Apparatus for Producing Interpolated Chromatic Values in a Sampled Color Image Signal") and L. Zhang and X. Wu, "Color Demosaicing The Directional Linear Minimum Mean Square Error Estimation," IEEE Trans. on Imaging Processing, 2005.

In particular, the efficient demosaicing method follows the assumptions that the color-difference signals between a green pixel and a red pixel at the same location and between a green pixel and the blue pixel at that location are low pass signals and that the second order gradients of different color components are similar. Edge-adaptiveness is also built in the efficient demosaicing process to better handle edge reconstruction. As a result, the efficient demosaicing process is cheaper to implement than the statistical demosaicing methods, but produces similar images that are better than popular adaptive interpolation processes in handling color artifacts and noise.

In one aspect, logically, the efficient demosaicing method includes two reconstruction processes. First, missing green pixels are reconstructed after estimating green-red color difference signals and green-blue color difference signals that are used in the reconstruction. Second, missing red and blue pixels are constructed using the color difference signals. Thus, the two reconstruction processes create a full resolution frame of pixels. A full resolution frame of pixels has a red pixel, a green pixel, and a blue pixel at each location in the frame. In one aspect, the full resolution frame of pixels is sent to a display unit for display.

Contrast enhanced images make it easier for surgeons to differentiate critical structures, such as blood vessels from surrounding tissues, when viewing a surgical site on a display of a surgical system. In surgical imaging, the predominant color is red for both tissues and blood vessels, making it hard for surgeons to differentiate critical structures from surrounding tissues. In addition, the red color component has lower contrast compared to green and blue color components due to tissue scattering of light that is especially true in close-range imaging. This makes it even harder to differentiate fine structures from surrounding tissues. Typically, compared to the blue component, the green component has a better signal-to-noise ratio due to sensor sensitivity.

In one aspect, the efficient demosaicing process includes local contrast enhancement. When the efficient demosaicing process includes contrast enhancement, the process is sometimes referred to as an enhanced demosaicing process. The key idea of enhancing image contrast is to build and boost a brightness component, e.g., a luminance component Y, from the green component, and build chromatic components, e.g., UV (or Cb, Cr) components, from all of the red, green, and blue color components.

In this aspect, logically, the enhanced demosaicing method includes three processes. First, missing green pixels are reconstructed after estimating green-red color difference signals and green-blue color difference signals that are used in the reconstruction. Second, each of green pixels is transformed to a brightness pixel by scaling the green pixel. Third, the missing red and blue pixels are not reconstructed. Instead, the green-red color difference signals and the green-blue color difference signals are transformed into chromatic component pixels. Following completion of the reconstruction, a full resolution frame of pixels is obtained, e.g., a frame with a Y pixel, a U pixel, and a V pixel at each location in the frame. In one aspect, this full resolution frame of pixels is sent to a display unit for display.

FIG. 2 is a schematic illustration of part of a teleoperated surgical system 200, such as a minimally invasive surgical system, e.g., the da Vinci® Surgical System. There are other components, parts, cables etc. associated with system 200 and with the da Vinci® Surgical System, but these are not illustrated in FIG. 2 to avoid detracting from the disclosure.

In this aspect, surgical system 200 includes an illuminator 215 (FIG. 2) that is coupled to a stereoscopic endoscope 212. In one aspect, illuminator 215 generates white light.

In one example, three color components make up white light illumination, i.e., white light includes first color component C1, second color component C2, and third color component C3. Each of the three-color components C1, C2, C3 is a different visible color component, e.g., a red color component, a green color component, and a blue color component.

The use of three visible color components C1, C2, C3 to make up white light illumination is illustrative of a plurality of such illumination components and is not intended to be limiting. Also, first, second, and third are used only as adjectives to distinguish between the different color components and are not intended to imply that any wavelength or frequency spectrum is associated with a particular color component.

In one aspect, illuminator 215 includes a source for each of the different visible color illumination components in the plurality of visible color illumination components of white light. For a red-green-blue implementation, in one example, the sources are light emitting diodes (LEDs), a red LED, two green LEDs and a blue LED.

The use of LEDs in illuminator 215 is illustrative only and is not intended to be limiting. Illuminator 215 could also be implemented with multiple laser sources instead of LEDs, for example. Alternatively, illuminator 215 could use a Xenon lamp with an elliptic back reflector and a band pass filter coating to create broadband white illumination light. The use of a Xenon lamp also is illustrative only and is not intended to be limiting. For example, a high-pressure mercury arc lamp, other arc lamps, or other broadband light sources may be used.

The use of an illuminator that is removed from endoscope 212 is also illustrative and not intended to be limiting. In some aspects, the illuminator could be mounted on or in the distal end of endoscope 212, for example.

In the aspect of FIG. 2, the light from illuminator 215 is directed into an illumination channel 216. The light passes through illumination channel 216 to another illumination channel in stereoscopic endoscope 212 that in turn directs the light to surgical site 203. Thus, in this aspect, surgical site 203 is illuminated by the white light.

The reflected white light from surgical site 203 (FIG. 2) is passed by the stereoscopic optical channels-a left channel and a right channel—in endoscope 212 to image capture system 220. Image capture system 220, in this aspect, includes a left image capture unit 221 that includes a first single-chip image capture sensor 225 with a first Bayer color filter array 223 and a right image capture unit 222 that includes a second single-chip image capture sensor 226 with a second Bayer color filter array 224. Each of Bayer color filter arrays 223 and 224 has pixel layout 100 (FIG. 1A).

Left image capture unit 221 captures a left frame and right image capture unit 222 captures a right frame. Both frames have the pixel layout of FIG. 1A. Camera control units 231 and 232 may be a single dual controller unit, or may be two separate controller units. Camera control units 231 and 232 receive signals from a system process module 263 that controls gains, controls capturing frames, and controls transferring captured frames to image processing system 240. Typically, system process module 263 with camera control units 231 and 232 controls the frequency at which the frames are captured. System process module 263 represents the various controllers including the vision system controllers in system 200.

Image processing system 240 includes, in one aspect, left demosaic module 243, left image processing system 241, right demosaic module 244, and right image processing system 242. In the following example, the processing performed by left image processing system 241 and by right image processing system 242 is the same. Similarly, the processing performed by left demosaic module 243 and by right demosaic module 244 is the same.

Thus, in the following description when an aspect of the efficient demosaicing process is described the process applies to both the left and the right channels. The description is not repeated for each of the left and right channels because the configuration and operation of the two channels is the same. Also, the processing of a single acquired color component frame is described. The processing performed on the single frame is performed repeatedly on each of the captured frames, i.e., a video sequence is generated.

The use of a stereoscopic endoscope with left and right processing channels also is illustrative only and is not intended to be limiting. The efficient demosaicing process and the efficient demosaicing process with local contrast enhancement can be used in any system that includes an image capture unit with an image capture sensor and a color filter array. Also, the inclusion of demosaic modules 243, 244 in image processing system 240 is illustrative only and is not intended to be limited. When demosaic modules 243, 244 are implemented in hardware, demosaic modules 243 and 244 can be included in image capture units 221 and 222.

Image processing system 240 can implement a variety of techniques to improve the quality of the images that are sent to stereoscopic display unit 250 in the surgeons control console. Optional image processing module 260 receives processes images from image processing system 240 prior to display on stereoscopic display unit 250. Optional image processing module 260 is equivalent to image processing modules in prior art teleoperated surgical systems and so is not considered in further detail.

Prior to considering efficient demosaicing module 243 further, it is helpful to understand the coordinate system of frame 100 and of the blocks of pixels described below. Each frame and each block has rows of pixels and columns of pixels. For example, frame 100 could have 1080 rows of 1920 pixels. A horizontal location x of a pixel within a frame is a value on an x-axis and a vertical location y of that pixel is represented by a value on the y-axis. The pixel at location (x, y) is the pixel that is currently being processed and is referred as the current pixel. In the example of a frame with 1920 by 1080 pixels, the value of x ranges from 0 to 1919, and the value of y ranges from 0 to 1079.

Frame 100 is a frame of raw pixels and has one pixel at each location in the frame. The efficient demosaicing process generates a new frame of pixels. The number of locations in frame 100 and the new frame typically are the same. However, the new frame has three pixels at each location in that frame.

A pixel is measured, in one aspect, with a value ranging from zero to 255, where zero is no light and 255 is maximum intensity. The range of values used herein is for illustration only and are not intended to be limiting. As is known to those knowledgeable in the field, a pixel with a value ranging from zero to 255 is stored as one byte of data. If more bytes of data are used for a pixel, the number of possible values changes.

Figure 3:
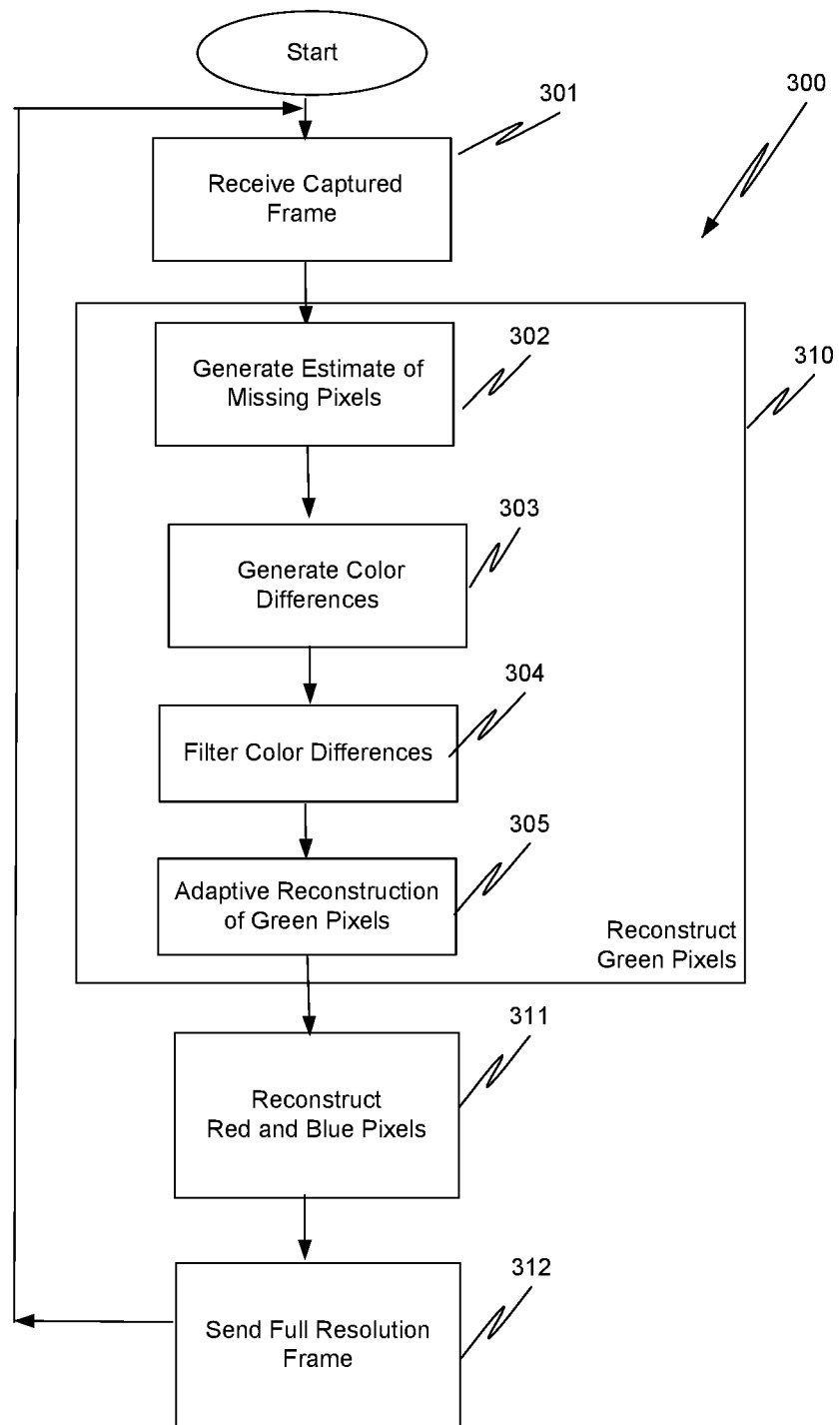
FIG. 3 is a process flow diagram of the efficient demosaicing process performed by the demosaicing modules of FIG. 2.

FIG. 3 is a process flow diagram of an EFFICIENT DEMOSAICING process 300 that is performed by demosaic module 243. Sometimes, EFFICIENT DEMOSAICING process 300 is referred to as process 300. In RECEIVE CAPTURED FRAME process 301, demosaic module 243, sometimes referred to as module 243, receives a frame of pixels from image capture unit 221. The pixels in the received frame have the pixel layout of frame 100 (FIG. 1A) due to Bayer color filter array 223.

In RECONSTRUCT GREEN PIXELS process 310, sometimes referred to as process 310, demosaic module 243 reconstructs missing green pixels so that all locations in frame 100G (FIG. 1B) have a green pixel value. In frame 100G, green pixels that were captured by image capture sensor 225 are represented by "G". As explained more completely below, GENERATE ESTIMATE OF MISSING PIXELS process 302 generates a horizontal estimated pixel and a vertical estimated pixel for each pixel location in received frame 100. Sometimes GENERATE ESTIMATE OF MISSING PIXELS process 302 is referred to as process 302.

Next GENERATE COLOR DIFFERENCES process 303 generates horizontal and vertical color difference signals, i.e., horizontal and vertical green-red color difference signals and horizontal and vertical green-blue color difference signals. Sometime these color difference signals are referred to as raw color difference signals or as color differences. After the color difference signals are available, FILTER COLOR DIFFERENCES process 304 filters each color difference signal to generate filtered color difference signals, sometimes referred to as filtered color differences.

At each location missing a green pixel in frame 100G (FIG. 1), ADAPTIVE RECONSTRUCTION OF GREEN PIXELS process 305, sometimes referred to as process 305, generates a reconstructed green pixel g for the location. Herein, when it is stated that a reconstructed green pixel g is generated, it means that a value of the pixel is generated which represents the intensity of that pixel.

Initially, in one aspect, process 305 generates a horizontal local edge estimator and a vertical local edge estimator for the missing green pixel. The relationship between the two local edge estimators is used to select either one of the horizontal filtered color difference signal and the vertical filtered color difference signal, or a combination of the horizontal and filtered color difference signals in reconstructing missing green pixel. The filtered color difference signal selected is the one that has the least edge effects. This color difference signal is used in reconstructing the missing green pixel g. Process 305 is adaptive, because the local edge characteristics at each pixel location are used in determining how to reconstruct the missing green pixel. Specifically, the process adapts to the edge conditions at each pixel location in frame 100.

When process 305 is completed, each location in the frame has either a green pixel G or a reconstructed green pixel g. Following completion of process 305, processing transfers to RECONSTRUCT RED AND BLUE PIXELS process 311, sometimes referred to as process 311. Process 311 reconstructs each missing blue pixel and each missing red pixel.

At each location missing a red pixel in frame 100R (FIG. 1C), RECONSTRUCT RED AND BLUE PIXELS process 311 reconstructs red pixels so that all these locations have a reconstructed red pixel r. In frame 100R, red pixels that were captured by image capture sensor 225 are represented by "R," and are sometimes referred to as original red pixel R. At each location missing a blue pixel in frame 100B (FIG. 1D), process 311 reconstructs blue pixels b so that all these locations have a reconstructed blue pixel b. In frame 100B, blue pixels that were captured by image capture sensor 225 are represented by "B," and are sometimes referred to as original blue pixel B. Note that while the same reference letter is used for pixels of the same color and same type (original or reconstructed), this denotes only the color of the pixel and not the value of the pixel.

RECONSTRUCT RED AND BLUE PIXELS process 311, in one aspect, uses the same adaptive process to reconstruct the red and blue pixels that was used to reconstruct the green pixels. In another aspect, for a blue pixel B, process 311 first averages the filtered color difference signals of the four red pixels R nearest blue pixel B. Process 311 then adds the average filtered color difference signal to the reconstructed green pixel g at the location to obtain the reconstructed red pixel r. Thus, each location with an original blue pixel B has original blue pixel B, a reconstructed green pixel g, and a reconstructed red pixel r.

In this aspect, for a red pixel R, process 311 first averages the filtered color difference signals of the four blue pixels B nearest red pixel R. Process 311 then adds the average filtered color difference signals to the reconstructed green pixel g at the location to obtain the reconstructed blue pixel b. Thus, each location with an original red pixel R has original red pixel R, a reconstructed green pixel g, and a reconstructed blue pixel b.

In this aspect, for a green pixel G, process 311 first averages the filtered horizontal color difference signals of the horizontal pixels nearest green pixel G. Process 311 then adds the average filtered horizontal color difference signals to green pixel G at the location to obtain one of a reconstructed red pixel r and a reconstructed blue pixel b. The pixel reconstructed depends on the color of the horizontal pixels adjacent to green pixel G. Process 311 next averages the filtered vertical color difference signals of the vertical pixels nearest green pixel G. Process 311 then adds the average filtered vertical color difference signal to green pixel G at the location to obtain the other of reconstructed red pixel r and reconstructed blue pixel b. Again, the pixel reconstructed depends on the color of the vertical pixels adjacent to green pixel G. Each location with an original green pixel G has a reconstructed red pixel r, original green pixel G, and a reconstructed blue pixel b.

Thus, demosaic module 243 reconstructs red, green, and blue pixels so that each location in frame 100 has not only the originally captured pixel, but also two reconstructed pixels as illustrated in new frame 400 (FIG. 4). Herein, reconstructed green pixels are represented by "g"; reconstructed red pixels are represented by "r"; and reconstructed blue pixels are represented by "b". While the same letter is used for a pixel at different locations in frame 400, this should be interpreted as indicating all the pixels with the same letter have the same value. Frame 400 is intended to show which pixels are reconstructed at each location.

Locations in frame 400 that have a captured green pixel G now also include a reconstructed red pixel r and a reconstructed blue pixel b. Locations in frame 400 that have a captured red pixel R now also include a reconstructed green pixel g and a reconstructed blue pixel b. Locations in frame 400 that have a captured blue pixel B now also include a reconstructed red pixel r and a reconstructed green pixel g. The following description provides greater detail on the reconstruction process for each of the reconstructed pixels.

SEND FULL RESOLUTION FRAME process 312 transfers frame 400 to left image processing system 241. Process 300 then starts demosaicing the next frame received from image capture unit 221.

Now, each of the processes in EFFICIENT DEMOSAICING process 300 is considered in further detail. In one aspect, process 300 of demosaic module 243 is implemented in hardware. In another aspect, module 243 includes computer program instructions that are stored in a memory and are executed on a processor. However, this is illustrative only and is not intended to be limiting. Demosaic module 243 may be implemented in practice by any combination of hardware, software that is executed on a processor, and firmware. Also, functions performed by demosaic module, as described herein, may be performed by one unit, or divided up among different components, each of which may be implemented in turn by any combination of hardware, software that is executed on a processor, and firmware. When divided up among different components, the components may be centralized in one location or distributed across system 200 for distributed processing purposes.

Figure 5A:
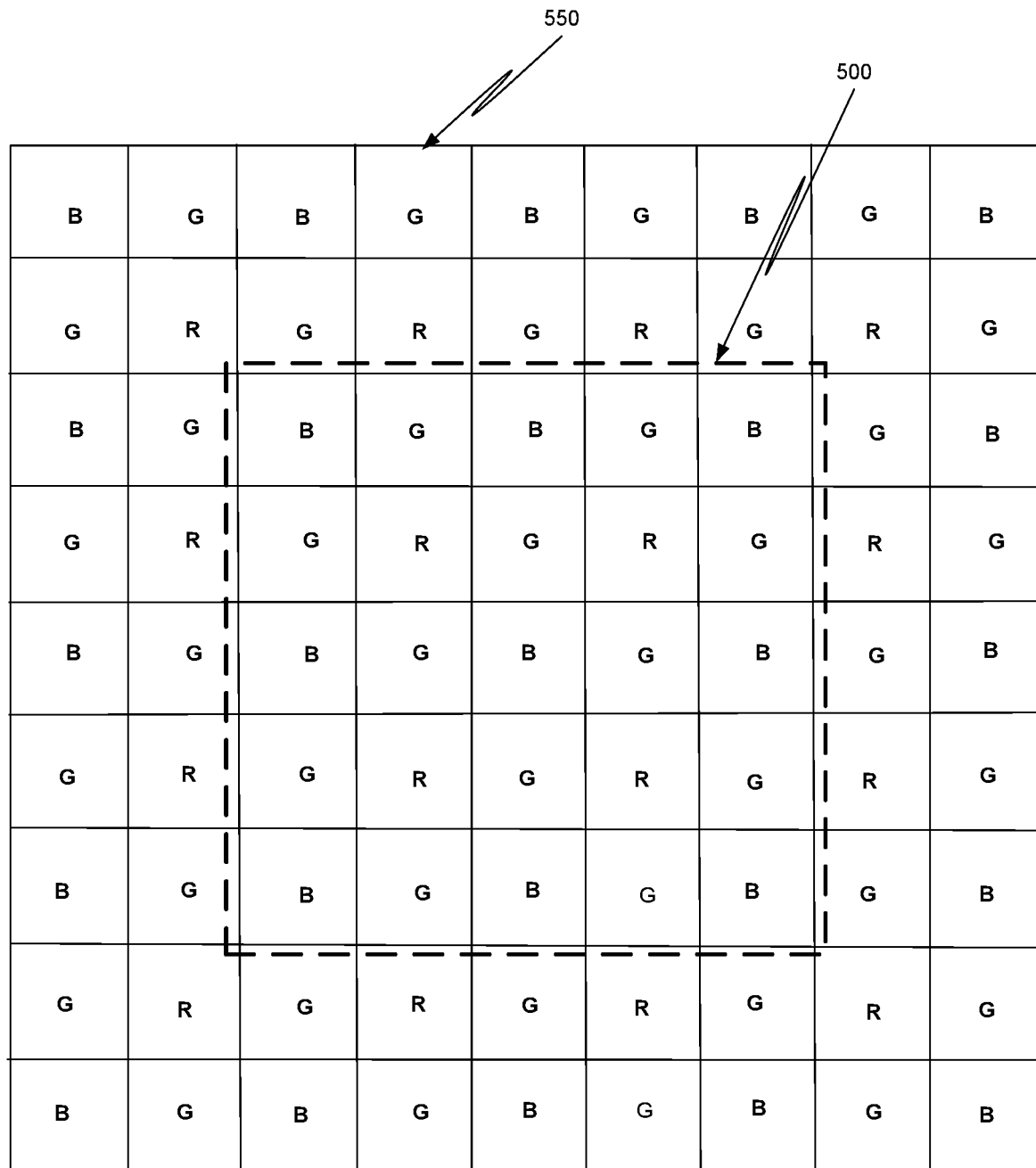
FIG. 5A is a schematic illustration of a block of raw pixel data within a frame received from an image capture unit with a Bayer color filter array.

FIG. 5A is a schematic illustration of a block of raw pixel data 550 within a frame received from an image capture unit with a Bayer color filter array. Within block 550, block 500 is considered in the following more detailed description of process 300. The processing of pixels in block 500, with the exception of the center pixel, requires raw pixel data in block 550 that is outside block 500. Block 550 includes sufficient raw pixel data that each pixel in block 500 can be processed as described below.

The outmost pixels of a received frame, i.e., the pixels in the two top and bottom rows of the received frame and the pixels in the two left most and right most columns in the received frame can be processed in a number of ways. The pixels values in the reconstructed pixels in adjacent rows and columns could be used in the outermost pixels, or raw pixel data can be reflected to create a border of pixels for the received frame and the outmost pixels processed as described below.

In RECONSTRUCT GREEN PIXELS process 310, GENERATE ESTIMATE OF MISSING PIXELS process 302, sometimes referred to as process 302, generates two pixels, a horizontal estimated pixel and a vertical estimated pixel for each pixel location. In one aspect, process 302 uses a second order series expansion to generate the estimated pixel values at a location. For example, when the current pixel is a green pixel G at location (x, y), process 302 uses the second order series expansion to generate estimated values for the red and blue pixels at location (x, y). When the current pixel is a red pixel R at location (x, y), process 302 uses the second order series expansion to generate estimated values for a green pixel at location (x, y). When the current pixel is a blue pixel B is at location (x, y), process 302 uses the second order series expansion to generate estimated values for a green pixel at location (x, y).

For each green pixel in a row of blue and green pixels, e.g., green pixel G at location 501 in row 510 (FIG. 5B), process 302 generates a vertical estimated red pixel r_v and a horizontal estimated blue pixel b_h. For each green pixel in a row of red and green pixels, e.g., a green pixel G at location 502 is in row 511, process 302 generates a horizontal estimated red pixel r_h and a vertical estimated blue pixel b_v.

For each red pixel, e.g., a red pixel R at location 503, process 302 generates a vertical estimated green pixel g_v and a horizontal estimated green pixel g_h. For each blue pixel, e.g., blue pixel B at location 504, process 302 generates a vertical estimated green pixel g_v and a horizontal estimated green pixel g_h.

Figure 5B:
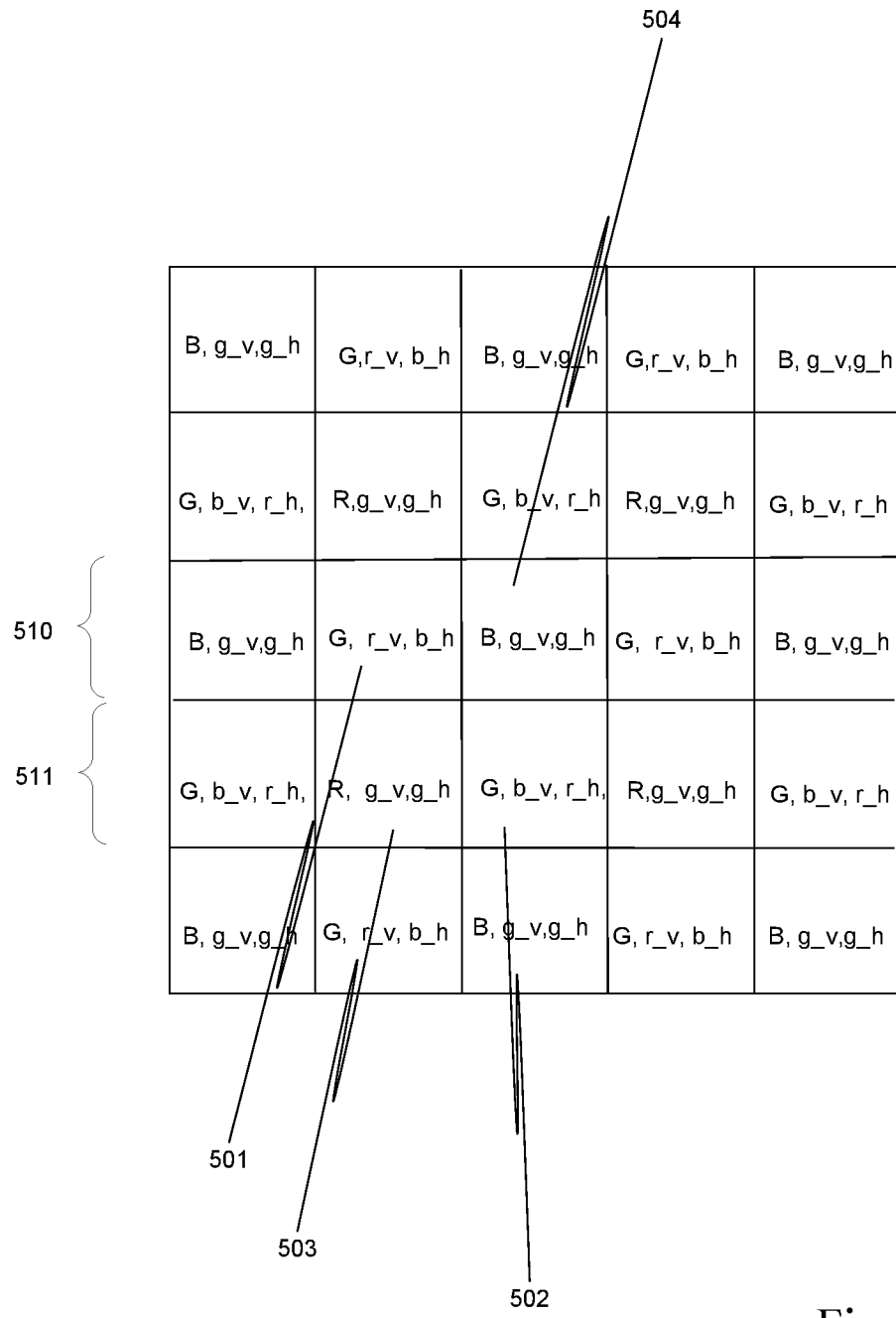
FIG. 5B illustrates the estimated pixels at each location in the block of FIG. 5A and the captured pixel at each location.

Thus, following completion of process 302, each location in block 500 has the information illustrated in FIG. 5B. In the drawings, a location in block 500 is bounded by a square. Following completion of process 302, processing transfers to GENERATE COLOR DIFFERENCES process 303, sometimes referred to as process 303.

Process 303 generates color difference signals, i.e., green-red color difference signals and green-blue color difference signals. For a green pixel G in a row of green and blue pixels, a horizontal green-blue color difference signal $GBdiff\_h(x, y)$ is defined as:

$$GBdiff\_h(x,y)=G(x,y)-b\_h(x,y)$$

For a green pixel G in a column of green and blue pixels, a vertical green-blue color difference signal $GBdiff\_v(x, y)$ is defined as:

$$GBdiff\_v(x,y)=G(x,y)-b\_v(x,y)$$

When a horizontal estimated green pixel $g\_h(x, y)$ that is estimated from a row of green pixels is used, horizontal green-blue color difference signal $GBdiff\_h(x, y)$ for a blue pixel B is defined as:

$$GBdiff\_h(x,y)=g\_h(x,y)-B(x,y)$$

When a vertical estimated green pixel g_v(x, y) that is estimated from a column of green pixels is used, vertical green-blue color difference signal GBdiff_v(x, y) for a blue pixel B, is defined as:

$$GBdiff\_v(x,y)=g\_v(x,y)-B(x,y)$$

For a green pixel G in a row of green and red pixels, a horizontal green-red color difference signal GRdiff_h(x, y) is defined as:

$$GRdiff\_h(x,y)=G(x,y)-r\_h(x,y)$$

For a green pixel G in a column of green and red pixels, a vertical green-red color difference signal GRdiff_v(x, y) is defined as:

$$GRdiff\_v(x,y)=G(x,y)-r\_v(x,y)$$

When a horizontal estimated green pixel g_h(x, y) that is estimated from a row of green pixels is used, horizontal green-red color difference signal GRdiff_h(x, y) for a red pixel R is defined as:

$$GRdiff\_h(x,y)=g\_h(x,y)-R(x,y)$$

When a vertical estimated green pixel g_v(x, y) that is estimated from a column of green pixels is used, vertical green-red color difference signal GRdiff_v(x, y) for a red pixel R is defined as:

$$GRdiff\_v(x,y)=g\_v(x,y)-R(x,y)$$

Thus, for green pixel G at location 501 in row 510 of green and blue pixels, process 303 generates horizontal green-blue color difference signal GBdiff_h(x, y) and vertical green-red color difference signal GRdiff_v(x, y). For blue pixel B at location 504 in row 510 of green and blue pixels, process 303 generates horizontal green-blue color difference signal GBdiff_h(x, y) and vertical green-blue color difference signal GBdiff_v(x, y).

For green pixel G at location 502 in row 511 of green and red pixels, process 303 generates horizontal green-red color difference signal GRdiff_h(x, y) and vertical green-blue color difference signal GBdiff_v(x, y). For red pixel R at location 503 in row 511 of green and red pixels, process 303 generates horizontal green-red color difference signal GRdiff_h(x, y) and vertical green-red color difference signal GRdiff_v(x, y).

Following completion of process of 303 the location of each green pixel G has one of a horizontal green-blue color difference signal GBdiff_h(x, y) and a horizontal green-red color difference signal GRdiff_h(x, y) and one of a vertical green-blue color difference signal GBdiff_v(x, y) and a vertical green-red color difference signal GRdiff_v(x, y). The location of each blue pixel B has a horizontal green-blue color difference signal GBdiff_h(x, y) and a vertical green-blue color difference signal GBdiff_v(x, y). The location of each red pixel R has a horizontal green-red color difference signal GRdiff_h(x, y) and vertical green-red color difference signal GRdiff_v(x, y). FIG. 5C shows the color difference signals for the pixels and estimated pixels in FIG. 5B.

Figure 6:
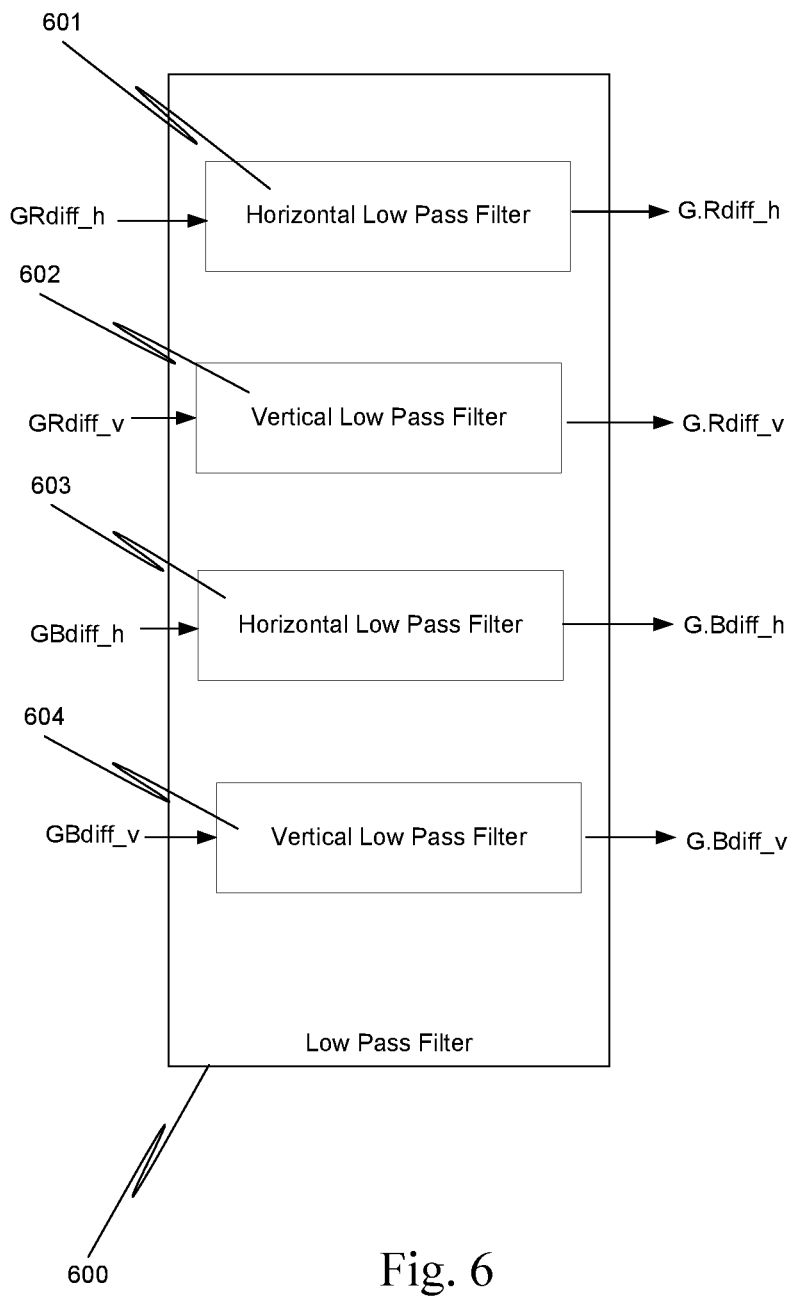
FIG. 6 is a schematic illustration of a low pass filter that is used, in one aspect, to filter the color difference signals.

After the color difference signals are available, FILTER COLOR DIFFERENCES process 304, sometimes referred to as process 304, low pass filters the color differences at each location using low pass filter 600 (FIG. 6). In one aspect, a nine-tap Gaussian filter is used.

Horizontal green-red color difference signal GRdiff_h(x, y) is filtered by horizontal low pass filter 601 to generate filtered horizontal green-red color difference signal G.Rdiff_h(x, y). Vertical green-red color difference signal GRdiff_v(x, y) is filtered by vertical low pass filter 602 to generate filtered vertical green-red color difference signal G.Rdiff_v(x, y).

Horizontal green-blue color difference signal GBdiff_h(x, y) is filtered by horizontal low pass filter 603 to generate filtered horizontal green-blue color difference signal G.Bdiff_h(x, y). Vertical green-blue color difference signal GBdiff_v(x, y) is filtered by vertical low pass filter 604 to generate filtered and vertical green-blue color difference signal G.Bdiff_v(x, y).

The use of four low pass filters in FIG. 6 is illustrative only and is not intended to be limiting. The low pass filtering can be implemented with more or less than four low pass filters. The number of filters used depends on the real-time requirements and cost. For example, a single low pass filter could be used, or four low pass filters could be used.

Figure 7:
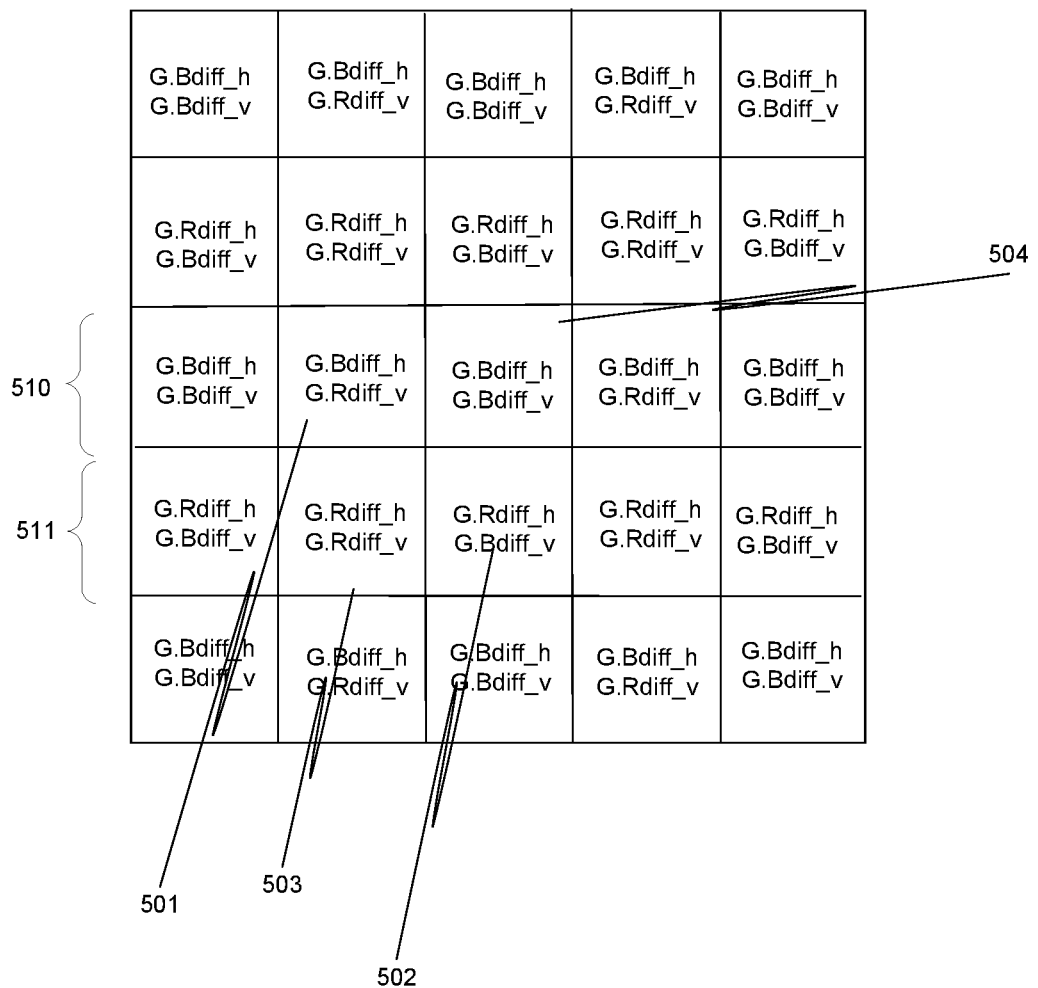
FIG. 7 illustrates the filtered color difference signals generated at each location in the block of FIG. 5A.

FIG. 7 illustrates the filtered signals at each location in block 500. Following completion of FILTER COLOR DIFFERENCES process 304 processing transfers to ADAPTIVE RECONSTRUCTION OF GREEN PIXELS process 305, sometimes referred to as process 305.

Figure 8:
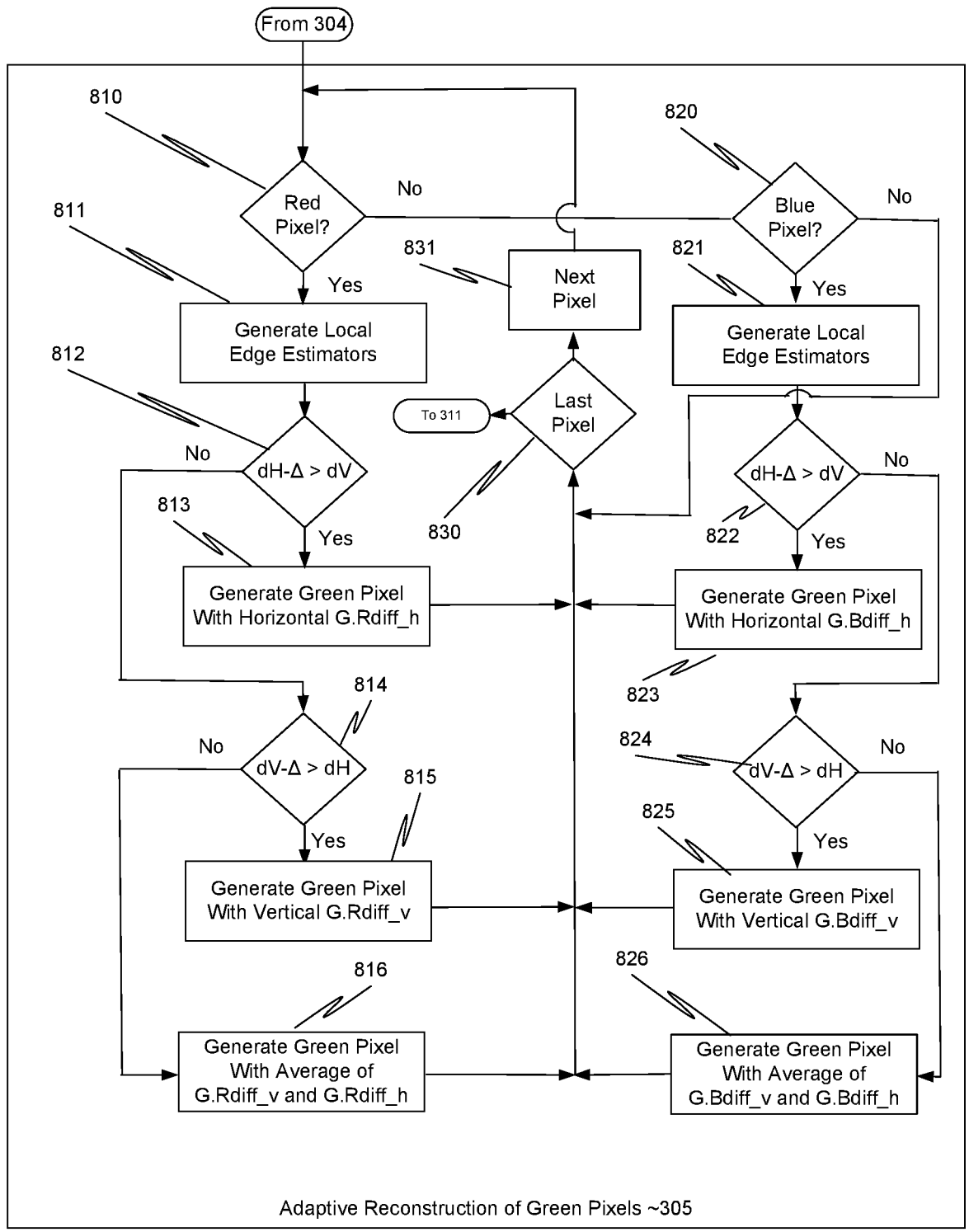
FIG. 8 is a more detailed process flow diagram of the adaptive reconstruction of green pixels process in FIG. 3.

FIG. 8 is a process flow diagram of process 305, in one aspect. The use of a linear process flow is illustrative only and is not intended to be limiting. In view of the following description, process 305 can be implemented in anyway that achieves each of the acts described. For example, process 305 could be implemented using two hardware pipelines-one pipeline that processes red pixels and a second pipeline that processes blue pixels. The red pixel pipeline generates a reconstructed green pixel g for each red pixel R, and the blue pixel pipeline generates a reconstructed green pixel g for each blue pixel B.

Alternatively, a single pipeline could be used. Examination of FIG. 8 shows that the same processes are used in the two pipelines and so could be implemented as a single pipeline. Herein, two pipelines, i.e., processes 811 to 816 and process 821 to 826, are used to assist in visualizing the processing of each captured pixel. However, processes 811 and 821 are equivalent. Check processes 812 and 822 are equivalent. Processes 813 and 823 are equivalent. Check processes 814 and 824 are equivalent. Processes 815 and 825 are equivalent, and processes 816 and 826 are equivalent.

Initially, RED PIXEL check process 810 determines whether the pixel at current location (x, y) is red pixel R. If the pixel is a red pixel R, RED PIXEL check process 810 transfer to GENERATE LOCAL EDGE ESTIMATORS process 811, sometimes referred to as process 811, and otherwise to BLUE PIXEL check process 820.

GENERATE LOCAL EDGE ESTIMATORS process 811 generates a vertical local edge estimator dV (of absolute value) and a horizontal local edge estimator dH (of absolute value), as described more completely below. Following generation of the local edge estimators, GENERATE LOCAL EDGE ESTIMATORS process 811 transfers to a first check process 812.

First check process 812 determines whether horizontal local estimator dH minus a robust factor $\Delta$ is larger than vertical local edge estimator dV. Stated in another way, check process 812 determines whether horizontal local estimator dH minus vertical local edge estimator dH is larger than robust factor $\Delta$. If horizontal local estimator dH minus vertical local edge estimator dV is larger than robust factor $\Delta$, there is a horizontal edge. Thus, check process 812 transfers to GENERATE GREEN PIXEL WITH FILTERED HORIZONTAL GREEN-RED DIFFERENCE process 813, sometimes referred to as process 813, and otherwise transfers to second check process 814. The usage of a small value robust factor Δ is chosen to prevent detection of false edges or a sudden shift, for example, from a vertical edge to horizontal edge, enabling a more robust process. In one aspect, robust factor Δ is normalized against the absolute pixel value. For example, robust factor Δ should be scaled up proportionally if the pixel goes from an eight-bit value to a ten-bit value.

In one aspect, the value of robust factor Δ is empirically determined based, for example, on noise levels and expected sharpness of edges in the captured images. For example, the local edge estimators at several typical locations-vertical edge, horizontal edge or no edge-were examined. In summary, the value of robust factor Δ that is selected depends on the image gradient values that are used in the edge estimators, hence the absolute value of a pixel (say 256/8 bit), how sharp an edge could be expected in an image, and noise level (larger noise implies larger delta) for typical images that are captured.

When check process 812 transfers to GENERATE GREEN PIXEL WITH FILTERED HORIZONTAL GREEN-RED DIFFERENCE process 813, the edge effect at location (x, y) is greater in the horizontal direction than in the vertical direction. Thus, the filtered horizontal green-red color difference signal provides a better estimate of the characteristics of green pixel g at location (x, y). GENERATE GREEN PIXEL WITH FILTERED HORIZONTAL GREEN-RED DIFFERENCE process 813 generates a reconstructed green pixel g at location (x, y) using the filtered horizontal green-red color difference signal G.Rdiff_h at location (x, y). Specifically, in one aspect:

$$g(x,y)=R(x,y)+G.\text{Rdiff}\_h(x,y)$$

Following generating reconstructed green pixel g(x, y), GENERATE GREEN PIXEL WITH FILTERED HORIZONTAL GREEN-RED DIFFERENCE process 813 transfers to LAST PIXEL check process 830.

If first check process 812 transfers to second check process 814, second check process 814 determines whether vertical local estimator dV minus robust factor Δ is larger than horizontal local edge estimator dH. Stated in another way, check process 814 determines whether vertical local estimator dV minus horizontal local edge estimator dH is larger than robust factor Δ. If vertical local estimator dV minus horizontal local edge estimator dH is larger than robust factor Δ, there is a vertical edge. Thus, check process 814 transfers to GENERATE GREEN PIXEL WITH FILTERED VERTICAL GREEN-RED DIFFERENCE process 815, sometimes referred to as process 815, and otherwise transfers to GENERATE GREEN PIXEL WITH AVERAGE OF FILTERED VERTICAL GREEN-RED DIFFERENCE AND FILTERED HORIZONTAL GREEN-RED DIFFERENCE process 816, sometimes referred to as process 816.

When check process 814 transfers to GENERATE GREEN PIXEL WITH FILTERED VERTICAL GREEN-RED DIFFERENCE process 815, the edge effect is greater in the vertical direction than in the horizontal direction at location (x, y). Thus, the filtered vertical green-red color difference signal provides a better estimate of the characteristics of green pixel g at location (x, y). GENERATE GREEN PIXEL WITH FILTERED VERTICAL GREEN-RED DIFFERENCE process 815 generates a reconstructed green pixel g at location (x, y) using the filtered vertical green-red color difference signal G.Rdiff_v at location (x, y). Specifically, in one aspect:

$$g(x,y)=R(x,y)+G.\text{Rdiff}\_v(x,y)$$

Following generating reconstructed green pixel g(x, y), GENERATE GREEN PIXEL WITH FILTERED VERTICAL GREEN-RED DIFFERENCE process 815 transfers to LAST PIXEL check process 830.

When check process 814 transfers to GENERATE GREEN PIXEL WITH AVERAGE OF FILTERED VERTICAL GREEN-RED DIFFERENCE AND FILTERED HORIZONTAL GREEN-RED DIFFERENCE process 816, the edge effects in the horizontal direction and vertical direction at location (x, y) are about equal, e.g., are different by an amount less than robust factor Δ. Thus, GENERATE GREEN PIXEL WITH AVERAGE OF FILTERED VERTICAL GREEN-RED DIFFERENCE AND FILTERED HORIZONTAL GREEN-RED DIFFERENCE process 816 generates a reconstructed green pixel g at location (x, y) using the average of filtered vertical green-red color difference signal G.Rdiff_v at location (x, y) and filtered horizontal green-red color difference signal G.Rdiff_h at location (x, y). Specifically, in one aspect:

$$g(x,y)=R(x,y)+((G.\text{Rdiff}\_v(x,y)+G.\text{Rdiff}\_h(x,y))/2)$$

Following generating reconstructed green pixel g(x, y), GENERATE GREEN PIXEL WITH AVERAGE OF FILTERED VERTICAL GREEN-RED DIFFERENCE AND FILTERED HORIZONTAL GREEN-RED DIFFERENCE process 816 transfers to LAST PIXEL check process 830.

When RED PIXEL check process 810 transfers to BLUE PIXEL check process 820, BLUE PIXEL check process 820 determines whether the pixel at current location (x, y) is a blue pixel B. If the pixel is a blue pixel B, BLUE PIXEL check process 820 transfer to GENERATE LOCAL EDGE ESTIMATORS process 821, sometimes referred to as process 821, and otherwise to LAST PIXEL check process 830.

GENERATE LOCAL EDGE ESTIMATORS process 821 generates vertical local edge estimator dV and horizontal local edge estimator dH, as described more completely below. Following generation of the local edge estimators, GENERATE LOCAL EDGE ESTIMATORS process 821 transfers to a third check process 822.

Third check process 822 determines whether horizontal local estimator dH minus robust factor Δ is larger than vertical local edge estimator dV. Stated in another way, check process 822 determines whether horizontal local estimator dH minus vertical local edge estimator dV is larger than robust factor Δ. If horizontal local estimator dH minus vertical local edge estimator dV is larger than robust factor Δ, there is a horizontal edge. Thus, check process 822 transfers to GENERATE GREEN PIXEL WITH FILTERED HORIZONTAL GREEN-BLUE DIFFERENCE process 823, sometimes referred to as process 823, and otherwise transfers to fourth check process 824.

When check process 822 transfers to GENERATE GREEN PIXEL WITH FILTERED HORIZONTAL GREEN-BLUE DIFFERENCE process 823, the edge effect at location (x, y) is greater in the horizontal direction than in the vertical direction. The filtered horizontal green-blue color difference signal provides a better estimate of the characteristics of green pixel g at location (x, y). Thus, GENERATE GREEN PIXEL WITH FILTERED HORIZONTAL GREEN-BLUE DIFFERENCE process 823 generates a reconstructed green pixel g at location (x, y) using the filtered horizontal green-blue color difference signal G.Bdiff_h at location (x, y). Specifically, in one aspect:

$$g(x,y)=B(x,y)+G.\text{Bdiff}\_h(x,y)$$

Following generating reconstructed green pixel g(x, y), GENERATE GREEN PIXEL WITH FILTERED HORIZONTAL GREEN-BLUE DIFFERENCE process 823 transfers to LAST PIXEL check process 830.

If third check process 822 transfers to fourth check process 824, fourth check process 824 determines whether vertical local estimator dV minus robust factor Δ is larger than horizontal local edge estimator dH. Stated in another way, check process 824 determines whether vertical local estimator dV minus horizontal local edge estimator dH is larger than robust factor Δ. If vertical local estimator dV minus horizontal local edge estimator dH is larger than robust factor Δ, there is a vertical edge. Thus, check process 824 transfers to GENERATE GREEN PIXEL WITH FILTERED VERTICAL GREEN-BLUE DIFFERENCE process 825, sometimes referred to as process 825, and otherwise transfers to GENERATE GREEN PIXEL WITH AVERAGE OF FILTERED VERTICAL GREEN-BLUE DIFFERENCE AND FILTERED HORIZONTAL GREEN-BLUE DIFFERENCE process 826, sometimes referred to as process 826.

When check process 824 transfers to GENERATE GREEN PIXEL WITH FILTERED VERTICAL GREEN-BLUE DIFFERENCE process 825, the edge effect is greater in the vertical direction than in the horizontal direction at location (x, y). Thus, the filtered vertical green-blue color difference signal provides a better estimate of the characteristics of green pixel g at location (x, y). GENERATE GREEN PIXEL WITH FILTERED VERTICAL GREEN-BLUE DIFFERENCE process 825 generates a reconstructed green pixel g at location (x, y) using the filtered vertical green-blue color difference signal G.Bdiff_v at location (x, y). Specifically, in one aspect:

$$g(x,y)=B(x,y)+G.\text{Bdiff}\_v(x,y)$$

Following generating reconstructed green pixel g(x, y), GENERATE GREEN PIXEL WITH FILTERED VERTICAL GREEN-BLUE DIFFERENCE process 825 transfers to LAST PIXEL check process 830.

When check process 824 transfers to GENERATE GREEN PIXEL WITH AVERAGE OF FILTERED VERTICAL GREEN-BLUE DIFFERENCE AND FILTERED HORIZONTAL GREEN-BLUE DIFFERENCE process 826, the edge effects in the horizontal direction and vertical direction at location (x, y) are about equal, e.g., a different by an amount less than robust factor Δ. Thus, GENERATE GREEN PIXEL WITH AVERAGE OF FILTERED VERTICAL GREEN-BLUE DIFFERENCE AND FILTERED HORIZONTAL GREEN-BLUE DIFFERENCE process 826 generates a reconstructed green pixel g at location (x, y) using the average of filtered vertical green-blue color difference signal G.Bdiff_v at location (x, y) and filtered horizontal green-blue color difference signal G.Bdiff_h at location (x, y).

$$g(x,y)=B(x,y)+((G.\text{Bdiff}\_v(x,y)+G.\text{Bdiff}\_h(x,y))/2)$$

Following generating reconstructed green pixel g(x, y), GENERATE GREEN PIXEL WITH AVERAGE OF FILTERED VERTICAL GREEN-BLUE DIFFERENCE AND FILTERED HORIZONTAL GREEN-BLUE DIFFERENCE process 826 transfers to LAST PIXEL check process 830.

When processing transfers to LAST PIXEL check process 830, check process 830 determines whether all the pixels in the frame have been processed. If all the pixels have been processed, check process 830 transfers to RECONSTRUCT RED AND BLUE PIXELS process 311 and otherwise transfers to NEXT PIXEL process 831. NEXT PIXEL process 831 moves the current pixel pointer from the current pixel to the next pixel in the frame and then transfers to RED PIXEL check process 810. Typically, this sequential process of GREEN first, and then RED and BLUE is not done sequentially pixel by pixel for the complete frame. It is a sequential process within a selected portion of the frame, e.g., a block of the frame, for real-time processing. In one aspect, this allows multiple blocks in a frame to be sequentially processed in parallel and so the processing can be done in real-time. The parallel processing of blocks within a frame is also applicable to the other processes described below.

Figure 9:
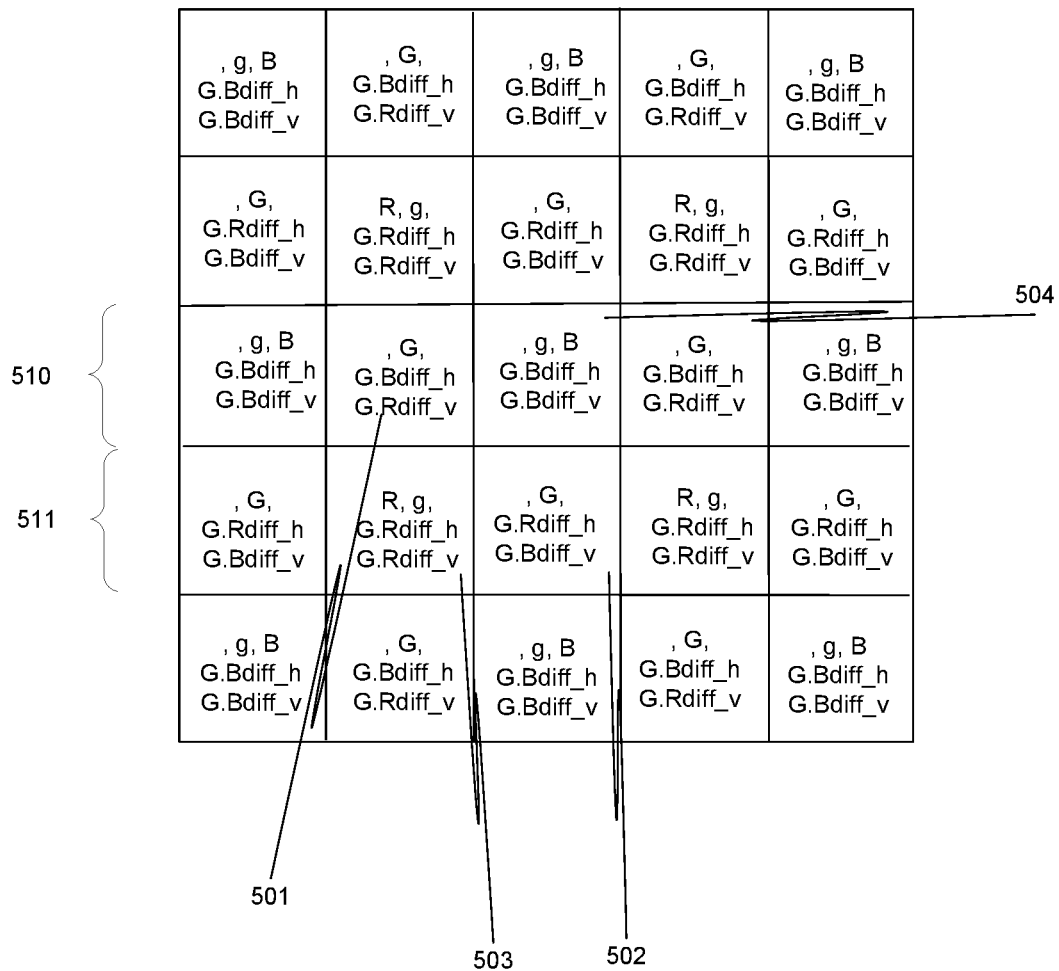
FIG. 9 illustrates the pixels and the filtered color difference signals at each location in the block of FIG. 5A following completion of the adaptive reconstruction of green pixels process in FIG. 8.

When check process 830 transfers to RECONSTRUCT RED AND BLUE PIXELS process 311, each location in the frame has either a green pixel G or a reconstructed green pixel g. FIG. 9 shows information available in pixel block 500 following completion of ADAPTIVE RECONSTRUCTION OF GREEN PIXELS process 305.

Figure 10:
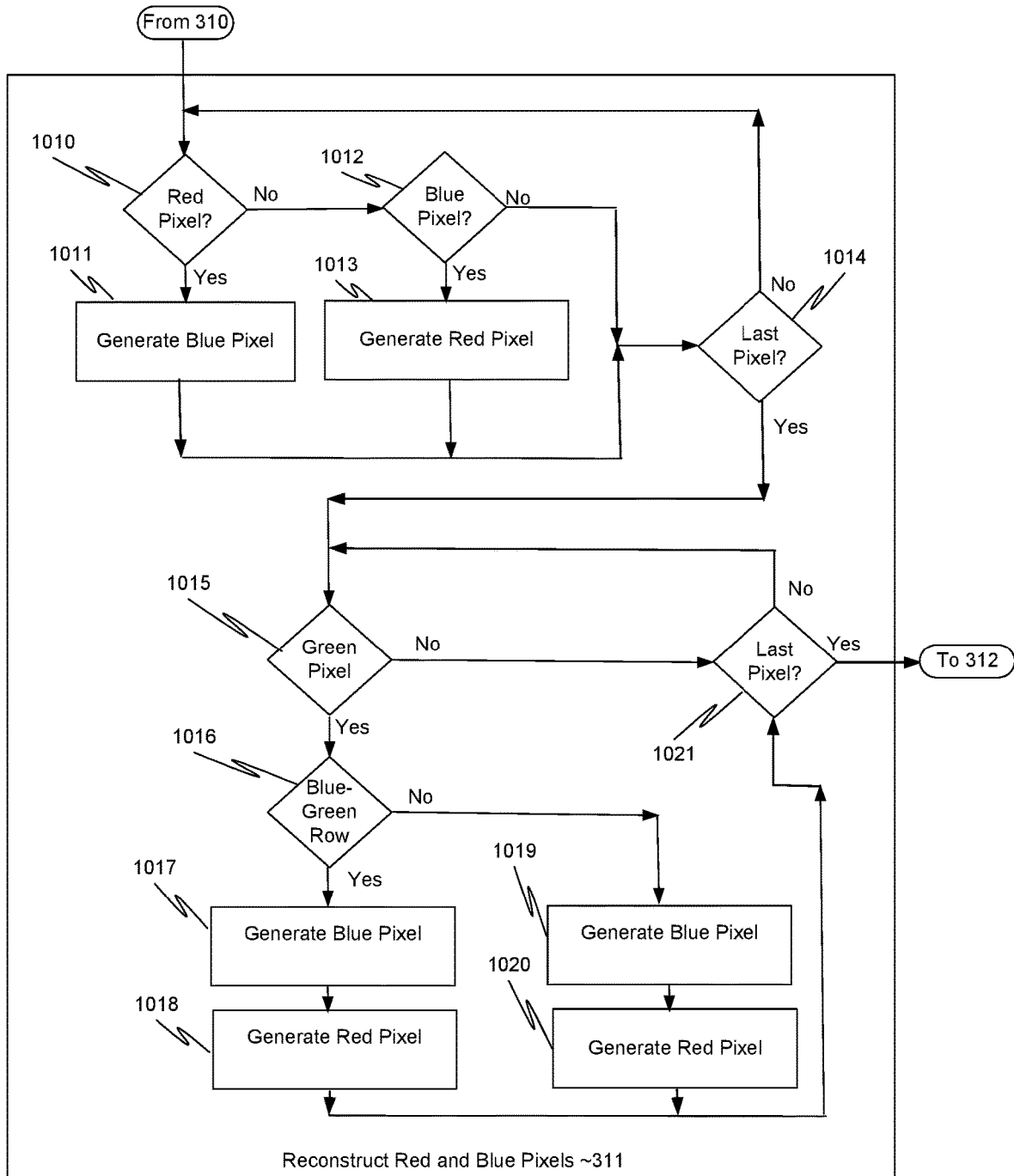
FIG. 10 is a more detailed process flow diagram of the reconstruct red and blue pixels process of FIG. 3.

RECONSTRUCT RED AND BLUE PIXELS process 311 can be implemented in a variety of ways. The generation of the missing green pixels is most critical and so the process has higher spatial resolution. The detailed spatial resolution is typically not required for the missing red and blue pixels and so a simpler reconstruction process can be used. FIG. 10 is a more detailed process flow diagram of one implementation of RECONSTRUCT RED AND BLUE PIXELS process 311. This diagram is illustrative only and is not intended to be limiting. The illustrated process flow and the order of the process flow is used for ease of discussion and is not intended to limit process 311 to either the specific acts or the specific sequence of acts shown. In view of this disclosure, one knowledgeable in the field can implement process 311 taking into consideration processor capability, available memory, timing requirements, etc.

In RECONSTRUCT RED AND BLUE PIXELS process 311, a reconstructed blue pixel b(x, y) is generated for each red pixel R(x, y), and then a reconstructed red pixel r(x, y) is generated for each blue pixel B(x, y). As described more completely below, each of these reconstructions use a sum of reconstructed green pixel g(x, y) and the average of color difference signals at the four diagonal neighboring pixels.

Following these reconstructions, each red pixel R(x, y) has a reconstructed green pixel and a reconstructed blue pixel. Each blue pixel B(x, y) has a reconstructed red pixel r(x, y) and a reconstructed green pixel g(x, y). Next, a reconstructed red pixel and r(x, y) and a reconstructed blue pixel b(x, y) are generated for each green pixel G(x, y).

Specifically, for the example of RECONSTRUCT RED AND BLUE PIXELS process 311 in FIG. 10, processing transfers from RECONSTRUCT GREEN PIXELS process 310 to RED PIXEL check process 1010. RED PIXEL check process 1010 determines whether the current pixel at location (x, y) is a red pixel R(x, y). If the current pixel at location (x, y) is a red pixel R(x, y), RED PIXEL check process 1010 transfers to GENERATE BLUE PIXEL process 1011, and otherwise transfers to BLUE PIXEL check process 1012.

GENERATE BLUE PIXEL process 1011 generates a reconstructed blue pixel b(x,y). Specifically, for a red pixel R(x, y), see FIG. 11A, reconstructed blue pixel b(x, y) is generated as a sum of reconstructed green pixel g(x, y) and the average of color difference signals (between the original blue pixel and the reconstructed green pixel) at the four diagonal neighboring pixels, i.e., $$b(x,y)=g(x,y)-\Delta GB\_R(x,y)$$

where $\Delta GB\_R(x, y)=-[(B(x-1,y+1)-g(x-1,y+1))+(B(x-1,y-1)-g(x-1,y-1))+(B(x+1,y-1)-g(x+1,y-1))+(B(x+1,y+1)-g(x+1,y+1))]/4$ Following generation of reconstructed blue pixel b(x, y), GENERATE BLUE PIXEL process 1011 transfers to LAST PIXEL check process 1014.

When RED PIXEL check process 1010 transfers to BLUE PIXEL check process 1012, check process 1012 determines whether the current pixel at location (x, y) is a blue pixel B(x, y). If the current pixel at location (x, y) is a blue pixel B(x, y), BLUE PIXEL check process 1012 transfers to GENERATE RED PIXEL process 1013, and otherwise transfers to LAST PIXEL check process 1014.

GENERATE RED PIXEL process 1013 generates a reconstructed red pixel r(x,y). Specifically, for an original blue pixel B(x, y), see FIG. 11B, a reconstructed red pixel r(x, y) is generated as the sum of reconstructed green pixel g(x, y) and the average of color difference signals (between the original red pixel and the reconstructed green pixel) at the four diagonal neighboring pixels, i.e., $$r(x,y)=g(x,y)-\Delta GR\_B(x,y)$$

where $\Delta GR\_B(x, y)=-[(R(x-1,y+1)-g(x-1,y+1))+(R(x-1,y-1)-g(x-1,y-1))+(R(x+1,y-1)-g(x+1,y-1))+(R(x+1,y+1)-g(x+1,y+1))]/4$ Following generation of reconstructed red pixel r(x, y), GENERATE RED PIXEL process 1013 transfers to LAST PIXEL check process 1014.

LAST PIXEL check process 1014 determines whether all the pixels in the frame have been processed. If all the pixels have been processed, LAST PIXEL check process 1014 resets the current pixel pointer to the start of the frame and then transfers to GREEN PIXEL check process 1015. Conversely, if all the pixels have not been processed, LAST PIXEL check process 1014 adjusts a current pixel pointer to the next pixel and then transfers to RED PIXEL check process 1010.

When LAST PIXEL check process 1014 transfers to GREEN PIXEL check process 1015, all reconstructed red pixels r(x, y) on original pixels B(x, y) and all reconstructed blue pixels b(x, y) original on red pixels R(x, y) have been generated, and so the reconstructed red pixels r(x, y) and the reconstructed blue pixels b(x, y) on original green pixels G(x, y) can be generated.

Thus, GREEN PIXEL check process 1015 determines whether the current pixel at location (x, y) is a green pixel G(x, y). If the current pixel at location (x, y) is a green pixel G(x, y), GREEN PIXEL check process 1015 transfers to BLUE-GREEN ROW check process 1016, and otherwise transfers to LAST PIXEL check process 1021.

The processing that is performed to generate the reconstructed red pixels r(x, y) and the reconstructed blue pixels b(x, y) on original green pixels G(x,y) depends on the color of the pixels surrounding original green pixel G(x, y). Thus, BLUE-GREEN ROW check process 1016 determines whether original green pixel G(x, y) is in a row of green and blue pixels. If original green pixel G(x, y) is in a row of green and blue pixels, check process 1016 transfers to a first GENERATE BLUE PIXEL process 1017 and otherwise transfers to a second GENERATE BLUE PIXEL process 1019.

When BLUE-GREEN ROW check process 1016 transfers to first GENERATE BLUE PIXEL process 1017, process 1017 generates a reconstructed blue pixel b(x,y) at location (x, y) of original green pixel G(x, y). Specifically, for original green pixel G(x, y), see FIG. 11C, a reconstructed blue pixel b(x, y) is generated as the sum of original green pixel G(x, y) and the average of color difference signals (between one of the original blue pixel or the reconstructed blue pixel from process 1011 and the reconstructed green pixel) at the four neighboring pixels, i.e., $$b(x,y)=G(x,y)-\Delta GB\_G(x,y)$$

where $\Delta GB\_G(x, y)=-([(B(x-1,y)-g(x-1,y))+(B(x+1,y)-g(x+1,y))+(b(x,y-1)-g(x,y-1))+(b(x,y+1)-g(x,y+1))])/4$ Upon completion, first GENERATE BLUE PIXEL process 1017 transfers processing to a first GENERATE RED PIXEL process 1018.

In first GENERATE RED PIXEL process 1018, a reconstructed red pixel r(x, y) is generated at location (x, y) of original green pixel G(x, y). Specifically, for original green pixel G(x, y), see FIG. 11C, a reconstructed red pixel r(x, y) is generated as the sum of original green pixel G(x, y) and the average of color difference signals (between one of the reconstructed red pixel from process 1013 or the original red pixel and the reconstructed green pixel) at the four neighboring pixels, i.e., $$r(x,y)=G(x,y)-\Delta GR\_G(x,y)$$

where $\Delta GR\_G(x, y)=-([(r(x-1,y)-g(x-1,y))+(r(x+1,y)-g(x+1,y))+(R(x,y-1)-g(x,y-1))+(R(x,y+1)-g(x,y+1))])/4$ Upon completion, first GENERATE RED PIXEL process 1018 transfers processing to LAST PIXEL check process 1021.

When BLUE-GREEN ROW check process 1016 transfers to second GENERATE BLUE PIXEL process 1019, process 1019 generates a reconstructed blue pixel b(x,y) at location (x, y) of original green pixel G(x, y). Specifically, for original green pixel G(x, y), see FIG. 11D, a reconstructed blue pixel b(x, y) is generated as the sum of original green pixel G(x, y) and the average of color difference signals (between one of the original blue pixel or the reconstructed blue pixel from process 1011 and the reconstructed green pixel) at the four neighboring pixels, i.e., $$b(x,y)=G(x,y)-\Delta GB\_G(x,y)$$

where $\Delta GB\_G(x, y)=-([(b(x-1,y)-g(x-1,y))+(b(x+1,y)-g(x+1,y))+(B(x,y-1)-g(x,y-1))+(B(x,y+1)-g(x,y+1))])/4$ Upon completion, second GENERATE BLUE PIXEL process 1019 transfers processing to a second GENERATE RED PIXEL process 1020.

In second GENERATE RED PIXEL process 1020, a reconstructed red pixel r(x, y) is generated at location (x, y) of original green pixel G(x, y). Specifically, for original green pixel G(x, y), see FIG. 11D, a reconstructed red pixel r(x, y) is generated as the sum of original green pixel G(x, y) and the average of color difference signals (between one of the reconstructed red pixel from process 1013 or the original red pixel and the reconstructed green pixel) at the four neighboring pixels, i.e., $$r(x,y)=G(x,y)-\Delta GR\_G(x,y)$$

where $\Delta GR\_G(x, y)=-([(R(x-1,y)-g(x-1,y))+(R(x+1,y)-g(x+1,y))+(r(x,y-1)-g(x,y-1))+(r(x,y+1)-g(x,y+1))])/4$ Upon completion, second GENERATE RED PIXEL process 1020 transfers processing to LAST PIXEL check process 1021.

LAST PIXEL check process 1021 determines whether all the pixels in the frame have been processed. If all the pixels have been processed, LAST PIXEL check process transfers to SEND FULL RESOLUTION FRAME process 312. Conversely, if all the pixels have not been processed, LAST PIXEL check process 1021 adjusts a current pixel pointer to the next pixel and then transfers to GREEN PIXEL check process 1015. When LAST PIXEL check process 1021 transfers to SEND FULL RESOLUTION FRAME process 312, each location in the frame has a complete set of red, green, and blue pixels.

As described above, GENERATE ESTIMATE OF MISSING PIXELS process 302 uses a second order series expansion in generating reconstructed pixels at a location in block 500. For example, when the current pixel is a green pixel G at location (x, y) (FIG. 12A or 12B), process 302 uses the second order series expansion to generate estimated values for the red and blue pixels at location (x, y). When the current pixel is a red pixel R at location (x, y) (FIG. 12C), process 302 uses the second order series expansion to generate estimated horizontal and vertical values for the green pixel at location (x, y). When the current pixel is a blue pixel B is at location (x, y) (FIG. 12D), process 302 uses the second order series expansion to generate horizontal estimated and vertical estimated pixel values for a green pixel at location (x, y).

The value of the pixel at location (x, y) is represented by a function f(x, y). A second order Taylor series expansion about x can be expressed as:

$$f(x+1,y)=f(x,y)+fx'(x,y)+fx''(x,y)/2 \text{ and}$$

$$f(x-1,y)=f(x,y)-fx'(x,y)+fx''(x,y)/2.$$

where the first order gradient fx'(x, y) can be approximated as:

$$fx'(x,y)=[f(x+1,y)-f(x-1,y)]/2, \text{ and}$$

where the second order gradient fx''(x, y) can be approximated as:

$$fx''(x,y)=[f(x+2,y)+f(x-2,y)-2*f(x,y)]/4.$$

Through simple manipulations, it can be shown that the interpolations f_h(x, y) and f_v(x, y) for missing pixels can be expressed as follows (using the second order Taylor series expansion) Horizontally along x:

$$f\_h(x,y)=[f(x+1,y)+f(x-1,y)]/2-[f(x+2,y)+f(x-2,y)-2*f(x,y)]/4$$

Vertically along y:

$$f\_v(x,y)=[f(x,y+1)+f(x,y-1)]/2-[f(x,y+2)+f(x,y-2)-2*f(x,y)]/4$$

The expressions are used in one aspect to generate vertical estimated red pixel r_v, horizontal estimated red pixel r_h, vertical estimated green pixel g_v, horizontal estimated green pixel g_h, vertical estimated blue pixel b_v, and vertical estimated blue pixel b_v in process 302.

These interpolations make sense based on the assumption that the second order gradients of different components are similar. For example, if location (x, y) is a green pixel (FIG. 12A or 12B) in a Bayer pattern color filter array, locations (x−1, y) and (x+1, y) are either red or blue pixels and (x−2, y) and (x+2, y) are green pixels. As a result, the interpolation would be good for either a missing red pixel or a missing blue pixel at location (x, y). When the pixel at location (x, y) is a red pixel (FIG. 12C), locations (x−1, y) and (x+1, y) are Green pixels and locations (x−2, y) and (x+2, y) are red pixels. As a result, the interpolation is good for a missing green pixel at location (x, y). The concepts in this paragraph and the previous paragraph are known to those knowledgeable in the field.

As described above, in ADAPTIVE RECONSTRUCTION OF GREEN PIXELS process 305, GENERATE LOCAL EDGE ESTIMATORS process 811 generates vertical local edge estimator dV and horizontal local edge estimator dH. The local estimators can be either a first order gradient or a combination of a first order gradient and a second order gradient.

For location (x, y), when horizontal local edge estimator dH is a first order gradient obtained using the above Taylor series expansion, horizontal local edge estimator dH is:

$$dH=|fx'(x,y)|=|[f(x+1,y)-f(x-1,y)]/2|$$

For location (x, y), when vertical local edge estimator dV is a first order gradient obtained using the above Taylor series expansion, vertical local edge estimator dV is:

$$dV=|fy'(x,y)|=|[f(x,y+1)+f(x,y-1)]/2|$$

For location (x, y), when horizontal local edge estimator dH is sum of the first order gradient obtained using the above Taylor series expansion and the above estimation of the second order gradient, horizontal local edge estimator dH is:

$$dH=|fx'(x,y)|+2*|fx''(x,y)|$$

$$dH=|[f(x+1,y)+f(x-1,y)]/2|+|[f(x+2,y)+f(x-2,y)-2*f(x,y)]/2|$$

For location (x, y), when vertical local edge estimator dV is sum of the first order gradient obtained using the above Taylor series expansion and the above estimation of the second order gradient, vertical local edge estimator dV is:

$$dV=|fy'(x,y)|+2*|fy''(x,y)|$$

$$dV=|[f(x,y+1)+f(x,y-1)]/2|+|[f(x,y+2)+f(x,y-2)-2f(x,y)]/2|$$

In another aspect, local contrast enhancement is implemented in the enhanced demosaicing process. Human perception of a color image is sensitive to the local brightness change, i.e., local contrast, of a color image. Thus, the demosaicing process with local contrast enhancement is designed to increase the local contrast while preserving the apparent global brightness to the extent possible, via discarding some or all of one or more color components of an original color image when determining a new brightness of pixels in a new contrast enhanced color image.

The efficient demosaicing process with local contrast enhancement, which is described more completely below, digitally enhances local contrast for surgical images based on physical properties of imaging and human perception of surgical image content. The contrast enhanced color images allow surgeons to more easily differentiate critical structures such as blood vessels from surrounding tissues.

In surgical imaging, the predominant color is red for both tissues and blood vessels, making it difficult for surgeons to differentiate critical structures from surrounding tissues. In addition, the red color component appears to be fuzzy compared to the green and blue color components, apparently due to relatively deeper tissue penetration of complex biological structures by the red color component. This is especially true in close-range imaging. This makes it even more difficult to differentiate fine structures from surrounding tissues. The efficient demosaicing process with local contrast enhancement described below enhances the color image contrast by removing, or at least reducing, the contrast contribution from the red and blue color components while keeping the true color of the color images unchanged.

In the following example, color images of surgical sites are considered. However, the use of surgical images is illustrative only and is not intended to be limiting. The methods described below for enhancement of contrast are also applicable to a system in which the response for one of a plurality of components in a color space is degraded. The degradation could be the result of poor optical system response, poor calibration of electronic components, failure of electronic components, etc. In each instance, the component in the color space associated with the degradation is not used in determining the brightness that provides enhanced contrast. For a more detailed description of contrast enhancement, see U.S. Patent Publication No. US 2012/0209287 A1 (disclosing "Method and Structure for Image Local Contrast Enhancement"), which is incorporated by reference.

The color components of the full resolution frame created in the enhanced demosaicing process are defined by a color space. Typical color spaces include: a color space that includes a red color component R, a green color component G, and a blue color component B, which is referred to as a RGB color space; a YUV color space that includes a luminance component Y and two chromatic components U and V; a YCbCr color space that includes a luminance component Y and two chromatic components Cb and Cr; and a color space that includes a hue component, a saturation component, and a brightness component. This list of color spaces and of the components included in the color spaces is illustrative only and is not intended to be limiting to these specific color spaces. Aspects of the invention may be applied in various color spaces.

The luminance components in the YUV and YCbCr color spaces and the brightness component in the hue, saturation, and brightness color space represent the apparent brightness of a pixel. The apparent brightness is defined by a grayscale. The grayscale has a range from black to white with varying shades of grey between black and white. The values of the grayscale, in one aspect, range from 0 to 255, where a value of zero represents black and a value of 255 represents white. Values between zero and 255 represent various shades of gray.

Herein, a brightness component refers to a component in a color space that is an apparent brightness and that is a grayscale component. The brightness component is not a color component because the brightness component conveys only brightness information and not color information. In color spaces with a brightness component, the color components are the components of the color space other than the brightness component and are referred to herein as chromatic components.

In the following example the YCbCr color space is used. However, this is illustrative only and is not intended to be limiting. The process described is applicable to any color space that includes a brightness component.

Figure 13:
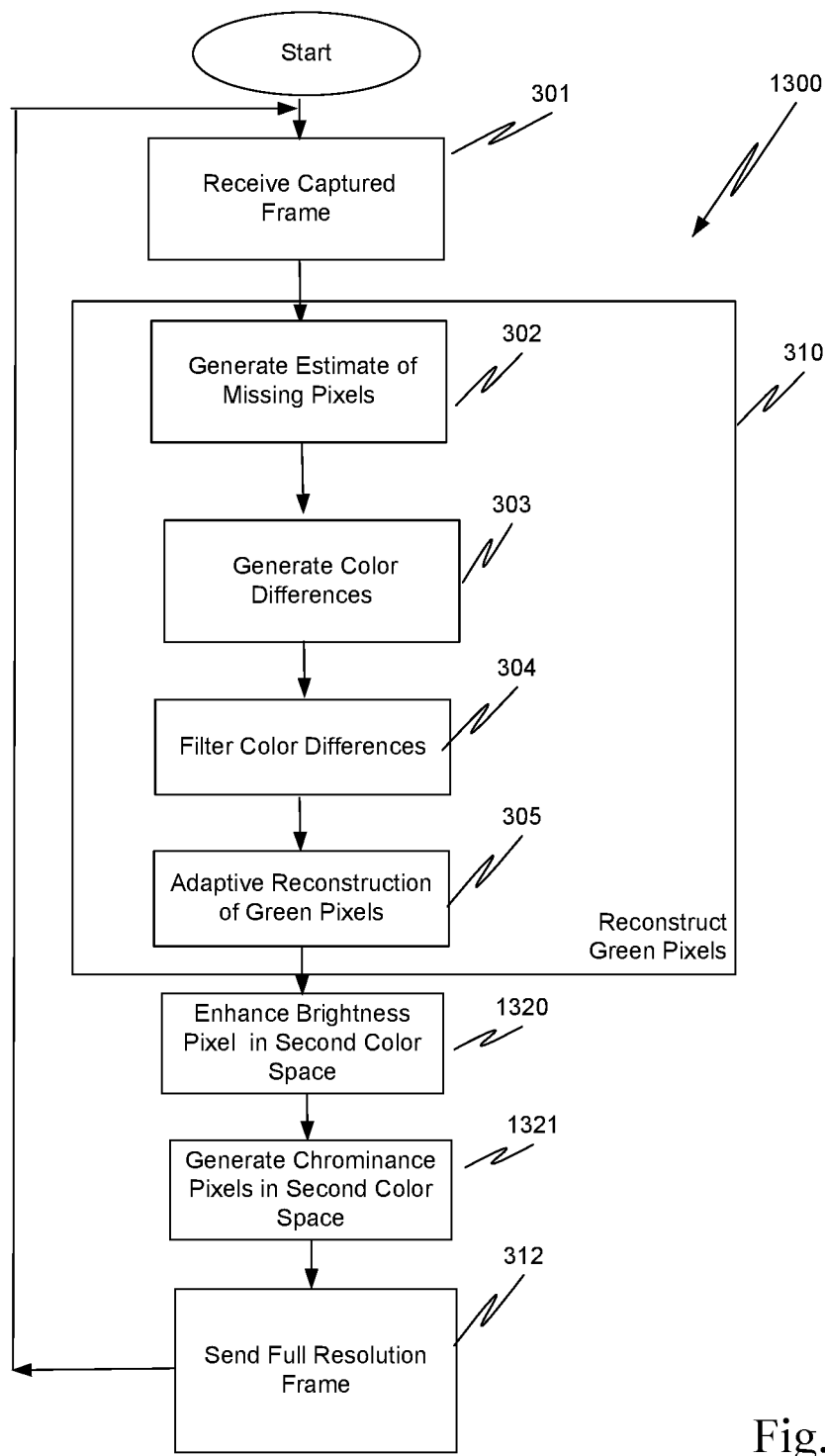
FIG. 13 is a process flow diagram of the efficient demosaicing process with local contrast enhancement performed by the demosaicing modules of FIG. 2.

FIG. 13 is a process flow diagram of one aspect of ENHANCED DEMOSAICING process 1300 with local contrast enhancement, sometimes referred to as process 1300. In process 1300, RECEIVE CAPTURED FRAME process 301 and RECONSTRUCT GREEN PIXELS process 310 are the same as described above with respect to FIG. 3 and so that description is not repeated for process 1300, but that description is incorporated by reference.

Following completion of process 310, the green pixels have been reconstructed and processing transfers to ENHANCE BRIGHTNESS PIXEL IN SECOND COLOR SPACE process 1320, sometimes referred to as process 1320.

Prior to considering process 1320, it is informative to consider a normal transformation from the RGB color space to the YCbCr color space. The transformation from the RGB color space to the YCbCr color space for a pixel is known. The transformation starts with a basic transform, which can be represented as:

$$Y=16+t11*R+t12*G+t13*B \quad (1a)$$

$$Cb=128+t21*R+t22*G+t23*B \quad (1b)$$

$$Cr=128+t31*R+t32*G+t33*B \quad (1c)$$

For example, t11=65.481, t12=128.553, t13=24.966; t21=−37.797, t22=−74.203, t23=112; and t31=112, t32=−93.786, t33=−18.214;

Definition (1a) is an example of a standards transformation that maps all color components of a first color space into a brightness component of a second color space. This transformation is defined by industry standards and the values of coefficients t11, t12, and t13 are defined by those industry standards. Therefore, definition (1a) is referred to as a standards transformation of color components in a first color space to a brightness component in a second color space.

To implement definition (1a) requires the red pixel and the blue pixel at each location, but the red and blue pixels at some locations are not available to process 1320. Thus, in process 1320, brightness component Ynew is defined as:

$$Ynew=16+S*t12*G \quad (2a)$$

where S is a scale factor. The contributions of the red and blue pixels to the brightness component are not used and the contribution of the green pixel to the brightness is scaled to compensate for the loss of the contribution of the red and blue pixels. Process 1320 uses definition (2a) to reconstruct a brightness pixel for each location in the frame. Following completion of process 1320, processing transfers to GENERATE CHROMINANCE PIXELS IN SECOND COLOR SPACE process 1321.

Scale factor S is empirically determined. For example, a RGB image is transformed to an image in the YCbCr color space using definitions (2a), (1b), and (1c). The transformation is done using a plurality of scale factors, e.g., 1.3, 1.4, and 1.5. The resulting images are reviewed by a group of individuals and the value of the scale factor for the image perceived as having the best overall contrast is selected as the value of scale factor S. In one aspect a value of 1.4 was used for scale factor S.

GENERATE CHROMINANCE PIXELS IN SECOND COLOR SPACE process 1321 skips the reconstruction of the red and blue pixels that would normally be used in the transformation to chrominance pixels. Instead, the transformation uses the filtered green-red color difference signals G.Rdiff and the filtered green-blue color difference signals G.Bdiff for each location in the captured frame 100. For example, direct computation from color difference signals to Cb and Cr can be derived from the standard transformation (1a)-(1c), with t11=65.481, t12=128.553, t13=24.966; t21=−37.797, t22=−74.203, t23=112; and t31=112, t32=−93.786, t33=−18.214:

$$Cb=128+(112/255)*G.Bdiff+(37.797/255)*G.Rdiff \quad (3a)$$

$$Cr=128+(112/255)*G.Rdiff+(18.214/255)*G.Bdiff \quad (3b)$$

Process 1321 applies this transformation to each location in the captured frame to generate the chrominance pixels at that location. However, the generation of the filtered green-red color difference signals G.Rdiff and the filtered green-blue color difference signals G.Bdiff is dependent upon the color of the captured pixel at the location.

In one aspect, the appropriate filtered green-red color difference signals G.Rdiff and the filtered green-blue color difference signals G.Bdiff are generated for a location and the above definition is used to generate the chrominance pixels. GENERATE CHROMINANCE PIXELS IN SECOND COLOR SPACE process 1321 can be implemented in a variety of ways. The generation of the missing green pixels is most critical and so the process has higher spatial resolution. The detailed spatial resolution is typically not required for the missing chrominance pixels and so a simpler reconstruction process can be used that uses color difference signals already available during processes 303 and 304.

Figure 14:
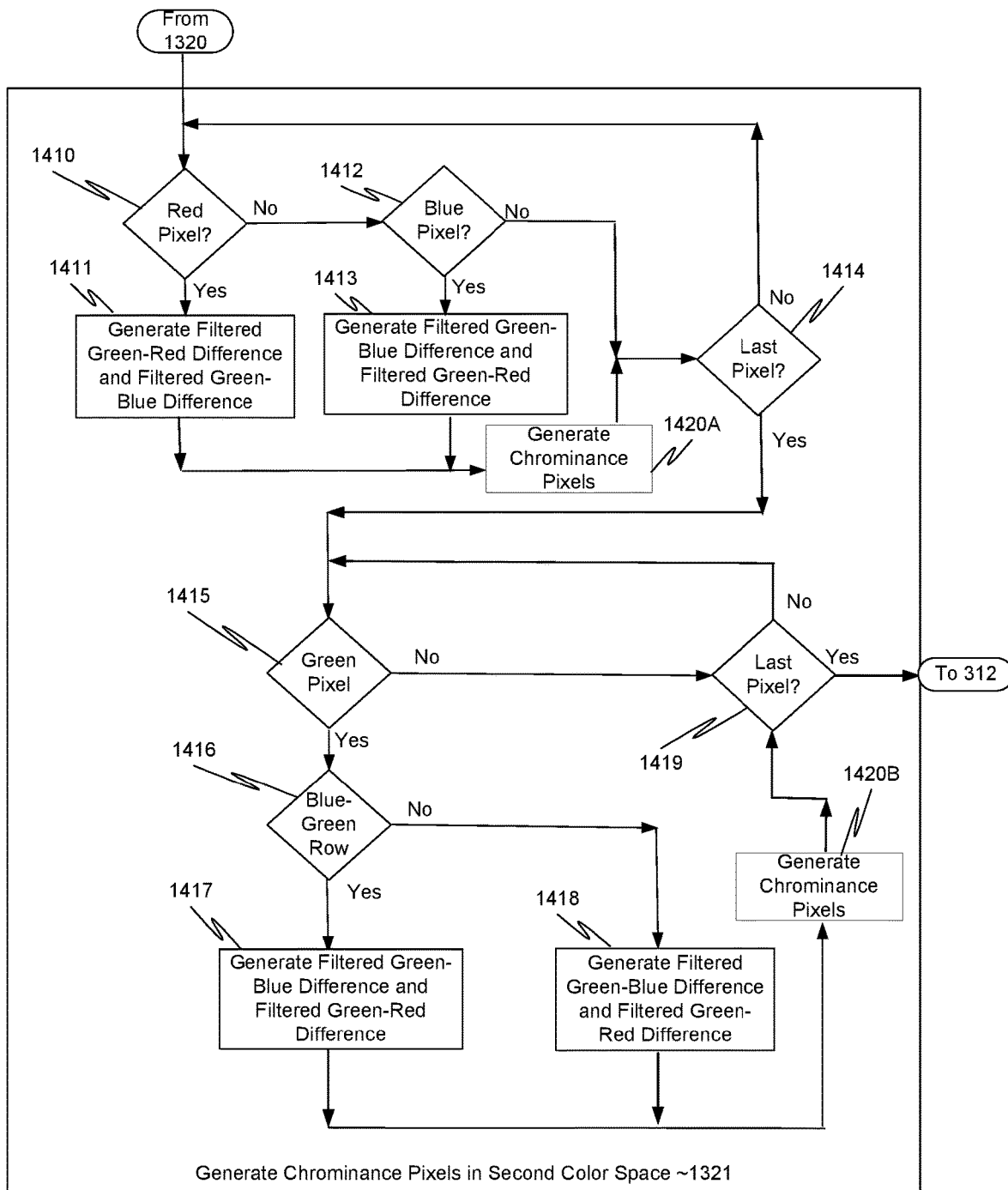
FIG. 14 is a more detailed process flow diagram of the generate chrominance pixels in a second color space process of FIG. 13.

FIG. 14 is a more detailed process flow diagram of one implementation of GENERATE CHROMINANCE PIXELS IN SECOND COLOR SPACE process 1321. This diagram is illustrative only and is not intended to be limiting. The illustrated process flow and the order of the process flow is used for ease of discussion and is not intended to limit process 1321 to either the specific acts or the specific sequence of acts shown. In view of this disclosure, one knowledgeable in the field can implement process 1321 taking into consideration processor capability, available memory, timing requirements, etc.

Recall that FIG. 9 presented the data available at each location upon completion of process 305. FIGS. 15A to 15D are blocks taken from FIG. 9 that represent the information used in this example of GENERATE CHROMINANCE PIXELS IN SECOND COLOR SPACE process 1321.

For the example of GENERATE CHROMINANCE PIXELS IN SECOND COLOR SPACE process 1321 in FIG. 14, processing transfers from ENHANCE BRIGHTNESS PIXEL IN SECOND COLOR SPACE 1320 to RED PIXEL check process 1410. RED PIXEL check process 1410 determines whether the current pixel at location (x, y) is a red pixel R(x, y). If the current pixel at location (x, y) is a red pixel R(x, y), RED PIXEL check process 1410 transfers to GENERATE FILTERED GREEN-RED DIFFERENCE AND FILTERED GREEN-BLUE DIFFERENCE process 1411, sometimes referred to as process 1411, and otherwise transfers to BLUE PIXEL check process 1412.

GENERATE FILTERED GREEN-RED DIFFERENCE AND FILTERED GREEN-BLUE DIFFERENCE process 1411 generates filtered green-red color difference signal G.Rdiff(x, y) and filtered green-blue color difference signal G.Bdiff(x, y) at location (x, y) of original red pixel R(x, y). Specifically, for a red pixel R(x, y), see FIG. 15A, filtered green-red color difference signal G.Rdiff(x, y) is generated as the average of the horizontal filtered green-red color difference signal G.Rdiff_h(x, y) and vertical filtered green-red color difference signal G.Rdiff_v(x, y), i.e., $$G.Rdiff(x,y)=(G.Rdiff\_h(x,y)+G.Rdiff\_v(x,y))/2$$

In process 1411, the filtered green-blue color difference signal G.Bdiff(x, y) is generated as the average of the color green-blue color difference signals at the four neighboring pixels, i.e., $$G.Bdiff(x,y)=(G\_Bdiff\_v(x-1,y)+G\_Bdiff\_v(x+1,y)+\\G\_Bdiff\_h(x,y-1)+G\_Bdiff\_h(x,y+1))/4$$

Upon completion, GENERATE FILTERED GREEN-RED DIFFERENCE AND FILTERED GREEN-BLUE DIFFERENCE process 1411 transfers to GENERATE CHROMINANCE PIXELS process 1420A.

GENERATE CHROMINANCE PIXELS process 1420A uses filtered green-red color difference signal G.Rdiff(x, y) and filtered green-blue color difference signal G.Bdiff(x, y) at location (x, y) of original red pixel R(x, y) in definitions (3a) and (3b) to generate chrominance pixels Cb and Cr at location (x, y). Upon completion GENERATE CHROMINANCE PIXELS process 1420A transfers to LAST PIXEL check process 1414.

When RED PIXEL check process 1410 transfers to BLUE PIXEL check process 1412, check process 1412 determines whether the current pixel at location (x, y) is a blue pixel B(x, y). If the current pixel at location (x, y) is a blue pixel B(x, y), BLUE PIXEL check process 1412 transfers to GENERATE FILTERED GREEN-BLUE DIFFERENCE AND FILTERED GREEN-BLUE DIFFERENCE process 1413, sometimes referred to as process 1413, and otherwise transfers to LAST PIXEL check process 1414.

GENERATE FILTERED GREEN-BLUE DIFFERENCE AND FILTERED GREEN-RED DIFFERENCE process 1413 generates filtered green-blue color difference signal G.Bdiff(x, y) and filtered green-red color difference signal G.Rdiff(x, y) at location (x, y) of original blue pixel B(x, y). Specifically, for a blue pixel B(x, y), see FIG. 15B, filtered green-blue color difference signal G.Bdiff(x, y) is generated as the average of the horizontal filtered green-blue color difference signal G.Bdiff_h(x, y) and vertical filtered green-blue color difference signal G.Bdiff_v(x, y), i.e., $$G.Bdiff(x,y)=(G.Bdiff\_h(x,y)+G.Bdiff\_v(x,y))/2$$

In process 1413, the filtered green-red color difference signal G.Rdiff(x, y) is generated as the average of the filtered green-red color difference signals at the four neighboring pixels, i.e., $$G.Rdiff(x,y)=(G\_Rdiff\_v(x-1,y)+G\_Rdiff\_v(x+1,y)+\\G\_Rdiff\_h(x,y+1)+G\_Rdiff\_h(x,y+1))/4$$

Upon completion, GENERATE FILTERED GREEN-BLUE DIFFERENCE AND FILTERED GREEN-RED DIFFERENCE process 1413 transfers to GENERATE CHROMINANCE PIXELS process 1420A.

GENERATE CHROMINANCE PIXELS process 1420A uses filtered green-red color difference signal G.Rdiff(x, y) and filtered green-blue color difference signal G.Bdiff(x, y) at location (x, y) of original blue pixel B(x, y) in definitions (3a) and (3b) to generate chrominance pixels Cb and Cr at location (x, y). Upon completion GENERATE CHROMINANCE PIXELS process 1420A transfers to LAST PIXEL check process 1414.

LAST PIXEL check process 1414 determines whether all the pixels in the frame have been processed. If all the pixels have been processed, LAST PIXEL check process 1414 resets the current pixel pointer to the start of the frame and then transfers to GREEN PIXEL check process 1415. Conversely, if all the pixels have not been processed, LAST PIXEL check process 1414 adjusts a current pixel pointer to the next pixel and then transfers to RED PIXEL check process 1410.

When LAST PIXEL check process 1414 transfers to GREEN PIXEL check process 1415, GREEN PIXEL check process 1415 determines whether the current pixel at location (x, y) is a green pixel G(x, y). If the current pixel at location (x, y) is a green pixel G(x, y), GREEN PIXEL check process 1415 transfers to BLUE-GREEN ROW check process 1416, and otherwise transfers to LAST PIXEL check process 1419.

The processing performed to generate filtered green-blue color difference signal G.Bdiff(x, y) and filtered green-red color difference signal G.Rdiff(x, y) at location (x, y) of original green pixel G(x, y) depends on the color of the pixels surrounding original green pixel G(x, y). Thus, BLUE-GREEN ROW check process 1416 determines whether original green pixel G(x, y) is in a row of green and blue pixels. If original green pixel G(x, y) is in a row of green and blue pixels, check process 1416 transfers to a second GENERATE FILTERED GREEN-BLUE DIFFERENCE AND FILTERED GREEN-RED DIFFERENCE process 1417, sometimes referred to as process 1417, and otherwise transfers to a third GENERATE FILTERED GREEN-BLUE DIFFERENCE AND FILTERED GREEN-RED DIFFERENCE process 1418, sometimes referred to as process 1418.

When BLUE-GREEN ROW check process 1416 transfers to second GENERATE FILTERED GREEN-BLUE DIFFERENCE AND FILTERED GREEN-RED DIFFERENCE process 1417, process 1417 generates filtered green-blue color difference signal G.Bdiff(x, y) and filtered green-red color difference signal G.Rdiff(x, y) at location (x, y) of original green pixel G(x, y). Filtered green-blue color difference signal G.Bdiff(x, y) is the average of the horizontal and vertical filtered green-blue color difference signals at location (x, y), where the vertical filtered green-blue color difference signal is the average of the filtered vertical green-blue color difference signals at the four diagonal neighboring pixels. Filtered green-red color difference signal G.Rdiff(x, y) is the average of the horizontal and vertical filtered green-red color difference signals at location (x, y), where the horizontal filtered green-red color difference signals is the average of the filtered horizontal green-red color difference signals at the four diagonal neighboring pixels.

Specifically, for original green pixel G(x, y), see FIG. 15C, process 1417 generates, $$G.Bdiff(x,y) = G.Bdiff\_h(x,y)/2 + (G.Bdiff\_v(x-1,y+1) + G\_Bdiff\_v(x-1,y-1) + G\_Bdiff\_v(x+1,y-1) + G\_Bdiff\_v(x+1,y+1))/8$$

and $$G.Rdiff(x,y) = G.Rdiff\_v(x,y)/2 + G.Rdiff\_h(x-1,y+1) + G\_Rdiff\_h(x-1,y-1) + G\_Rdiff\_h(x+1,y-1) + G\_Rdiff\_h(x+1,y+1))/8$$

Upon completion, second GENERATE FILTERED GREEN-BLUE DIFFERENCE AND FILTERED GREEN-RED DIFFERENCE process 1417 transfers to GENERATE CHROMINANCE PIXELS process 1420B.

GENERATE CHROMINANCE PIXELS process 1420B uses filtered green-red color difference signal G.Rdiff(x, y) and filtered green-blue color difference signal G.Bdiff(x, y) at location (x, y) of original green pixel G(x, y) in definitions (3a) and (3b) to generate chrominance pixels Cb and Cr at location (x, y). Upon completion GENERATE CHROMINANCE PIXELS process 1420B transfers to LAST PIXEL check process 1419.

When BLUE-GREEN ROW check process 1416 transfers to third GENERATE FILTERED GREEN-BLUE DIFFERENCE AND FILTERED GREEN-RED DIFFERENCE process 1418, process 1418 generates filtered green-blue color difference signal G.Bdiff(x, y) and filtered green-red color difference signal G.Rdiff(x, y) at location (x, y) of original green pixel G(x, y) (FIG. 15D). Filtered green-blue color difference signal G.Bdiff(x, y) is the average of the horizontal and vertical filtered green-blue color difference signals at location (x, y), where the horizontal filtered green-blue color difference signal is the average of the filtered vertical green-blue color difference signals at the four diagonal neighboring pixels. Filtered green-red color difference signal G.Rdiff(x, y) is the average of the horizontal and vertical filtered green-red color difference signals at location (x, y), where the vertical filtered green-red color difference signals is the average of the filtered horizontal green-red color difference signals at the four diagonal neighboring pixels.

Specifically, for original green pixel G(x, y), see FIG. 15D, process 1418 generates, $$G.Bdiff(x,y) = G.Bdiff\_v(x,y)/2 + (G.Bdiff\_h(x-1,y+1) + G\_Bdiff\_h(x-1,y-1) + G\_Bdiff\_h(x+1,y-1) + G\_Bdiff\_h(x+1,y+1))/8, \text{ and}$$

$$G.Rdiff(x,y) = G.Rdiff\_h(x,y)/2 + G.Rdiff\_v(x-1,y+1) + G\_Rdiff\_v(x-1,y-1) + G\_Rdiff\_v(x+1,y-1) + G\_Rdiff\_v(x+1,y+1))/8$$

Upon completion, second GENERATE FILTERED GREEN-BLUE DIFFERENCE AND FILTERED GREEN-RED DIFFERENCE process 1418 transfers to GENERATE CHROMINANCE PIXELS process 1420B.

GENERATE CHROMINANCE PIXELS process 1420B uses filtered green-red color difference signal G.Rdiff(x, y) and filtered green-blue color difference signal G.Bdiff(x, y) at location (x, y) of original green pixel G(x, y) in definitions (3a) and (3b) to generate chrominance pixels Cb and Cr at location (x, y). Upon completion GENERATE CHROMINANCE PIXELS process 1420B transfers to LAST PIXEL check process 1419.

LAST PIXEL check process 1419 determines whether all the pixels in the frame have been processed. If all the pixels have been processed, LAST PIXEL check process 1419 transfers to SEND FULL RESOLUTION FRAME process 312. Conversely, if all the pixels have not been processed, LAST PIXEL check process 1419 adjusts a current pixel pointer to the next pixel and then transfers to GREEN PIXEL check process 1415. When check process 1419 transfers to SEND FULL RESOLUTION FRAME process 312, each location in the frame has a complete set of Y, Cb, and Cr pixels.

As used herein, "first," "second," and "third" are adjectives used to distinguish between different color components and different elements. Thus, "first," "second," and "third" are not intended to imply any ordering of the components or the elements.

The above description and the accompanying drawings that illustrate aspects and embodiments of the present inventions should not be taken as limiting—the claims define the protected inventions. Various mechanical, compositional, structural, electrical, and operational changes may be made without departing from the spirit and scope of this description and the claims. In some instances, well-known circuits, structures, and techniques have not been shown or described in detail to avoid obscuring the invention.

Further, this description's terminology is not intended to limit the invention. For example, spatially relative terms—such as "beneath", "below", "lower", "above", "upper", "proximal", "distal", and the like—may be used to describe one element's or feature's relationship to another element or feature as illustrated in the figures. These spatially relative terms are intended to encompass different positions (i.e., locations) and orientations (i.e., rotational placements) of the device in use or operation in addition to the position and orientation shown in the figures. For example, if the device in the figures were turned over, elements described as "below" or "beneath" other elements or features would then be "above" or "over" the other elements or features. Thus, the exemplary term "below" can encompass both positions and orientations of above and below. The device may be otherwise oriented (rotated 90 degrees or at other orientations) and the spatially relative descriptors used herein interpreted accordingly. Likewise, descriptions of movement along and around various axes include various special device positions and orientations.

The singular forms "a", "an", and "the" are intended to include the plural forms as well, unless the context indicates otherwise. The terms "comprises", "comprising", "includes", and the like specify the presence of stated features, steps, operations, elements, and/or components but do not preclude the presence or addition of one or more other features, steps, operations, elements, components, and/or groups. Components described as coupled may be electrically or mechanically directly coupled, or they may be indirectly coupled via one or more intermediate components.

Memory refers to a volatile memory, a non-volatile memory, or any combination of the two. A processor is coupled to a memory containing instructions executed by the processor. This could be accomplished within a computer system, or alternatively via a connection to another computer via modems and analog lines, or digital interfaces and a digital carrier line.

Herein, a computer program product comprises a non-transitory medium configured to store computer readable code needed for any one or any combination of the operations described with respect to the demosaicing process or in which computer readable code for any one or any combination of operations described with respect to the demosaicing process is stored. Some examples of computer program products are CD-ROM discs, DVD discs, flash memory, ROM cards, floppy discs, magnetic tapes, computer hard drives, servers on a network and signals transmitted over a network representing computer readable program code. A non-transitory tangible computer program product comprises a non-transitory tangible medium configured to store computer readable instructions for any one of, or any combination of operations described with respect to the demosaicing process or in which computer readable instructions for any one of, or any combination of operations described with respect to the demosaicing process are stored. Non-transitory tangible computer program products are CD-ROM discs, DVD discs, flash memory, ROM cards, floppy discs, magnetic tapes, computer hard drives and other non-transitory physical storage mediums.

In view of this disclosure, instructions used in any one of, or any combination of operations described with respect to the enhance demosaicing method can be implemented in a wide variety of computer system configurations using an operating system and computer programming language of interest to the user.

All examples and illustrative references are non-limiting and should not be used to limit the claims to specific implementations and embodiments described herein and their equivalents. The headings are solely for formatting and should not be used to limit the subject matter in any way, because text under one heading may cross reference or apply to text under one or more headings. Finally, in view of this disclosure, particular features described in relation to one aspect or embodiment may be applied to other disclosed aspects or embodiments of the invention, even though not specifically shown in the drawings or described in the text.

What is claimed is:

1. A method comprising:
receiving a frame of raw pixels captured by an image capture sensor, a particular location in the frame of raw pixels including a captured color pixel value of a first color component of a first color space;
generating, for the particular location in the frame of raw pixels, a vertical color difference signal and a horizontal color difference signal using information from the frame of raw pixels;
determining that the particular location is missing a color pixel value of a second color component of the first color space;
generating, for the particular location in the frame of raw pixels, a reconstructed color pixel value of the second color component based on the vertical color difference signal and the horizontal color difference signal; and
transforming, for the particular location in the frame of raw pixels, the vertical color difference signal and the horizontal color difference signal of the particular location in the frame of raw pixels into chrominance pixel values in a second color space that is different from the first color space;
wherein transforming the vertical color difference signal and the horizontal color difference signal into the chrominance pixel values in the second color space comprises:
determining an average of the vertical color difference signal and the horizontal color difference signal; and
using the average of the vertical color difference signal and the horizontal color difference signal to determine the chrominance pixel values in the second color space.

2. The method of claim 1, wherein for the particular location:
the captured color pixel value is a captured green pixel value;
the horizontal color difference signal is the captured green pixel value minus a horizontal estimated blue pixel value; and
the vertical color difference signal is the captured green pixel value minus a vertical estimated red pixel value.

3. The method of claim 1, further comprising:
transforming, for the particular location in the frame of raw pixels, the captured color pixel value of the first color component to a brightness pixel value in the second color space.

4. The method of claim 3, wherein transforming the captured color pixel value of the first color component to the brightness pixel value in the second color space is performed without using a color pixel value of a second color component of the first color space.

5. The method of claim 4, wherein transforming the captured color pixel value of the first color component to the brightness pixel value in the second color space is performed without using a color pixel value of a third color component of the first color space.

6. The method of claim 1, further comprising:
generating, for the particular location in the frame of raw pixels and using information from the frame of raw pixels, a vertical estimated color pixel value of the first color component of the first color space and a horizontal estimated color pixel value of the first color component of the first color space;
wherein generating the vertical color difference signal and the horizontal color difference signal for the particular location in the frame of pixels uses the vertical estimated color pixel value and the horizontal estimated color pixel value.

7. A system comprising:
a memory storing instructions; and
one or more processors communicatively coupled to the memory and configured to execute the instructions to perform a process comprising:
receiving a frame of raw pixels captured by an image capture sensor, a particular location in the frame of raw pixels including a captured color pixel value of a first color component of a first color space;
generating, for the particular location in the frame of raw pixels, a vertical color difference signal and a horizontal color difference signal using information from the frame of raw pixels;
determining that the particular location is missing a color pixel value of a second color component of the first color space;
generating, for the particular location in the frame of raw pixels, a reconstructed color pixel value of the second color component based on the vertical color difference signal and the horizontal color difference signal; and
transforming, for the particular location in the frame of raw pixels, the vertical color difference signal and the horizontal color difference signal of the particular location in the frame of raw pixels into chrominance pixel values in a second color space that is different from the first color space;
wherein transforming the vertical color difference signal and the horizontal color difference signal into the chrominance pixel values in the second color space comprises:
determining an average of the vertical color difference signal and the horizontal color difference signal; and
using the average of the vertical color difference signal and the horizontal color difference signal to determine the chrominance pixel values in the second color space.

8. The system of claim 7, wherein for the particular location:
the captured color pixel value is a captured green pixel value;
the horizontal color difference signal is the captured green pixel value minus a horizontal estimated blue pixel value; and
the vertical color difference signal is the captured green pixel value minus a vertical estimated red pixel value.

9. The system of claim 7, wherein the process further comprises:
transforming, for the particular location in the frame of raw pixels, the captured color pixel value of the first color component to a brightness pixel value in the second color space.

10. The system of claim 9, wherein transforming the captured color pixel value of the first color component to the brightness pixel value in the second color space is performed without using a color pixel value of a second component of the first color space.

11. The system of claim 10, wherein transforming the captured color pixel value of the first color component to the brightness pixel value in the second color space is performed without using a color pixel value of a third color component of the first color space.

12. The system of claim 7, wherein the process further comprises:
generating, for the particular location in the frame of raw pixels and using information from the frame of raw pixels, a vertical estimated color pixel value of the first color component of the first color space and a horizontal estimated color pixel value of the first color component of the first color space;
wherein generating the vertical color difference signal and the horizontal color difference signal for the particular location in the frame of pixels uses the vertical estimated color pixel value and the horizontal estimated color pixel value.

13. A non-transitory computer-readable medium storing instructions executable by a processor to perform a process comprising:
receiving a frame of raw pixels captured by an image capture sensor, a particular location in the frame of raw pixels including a captured color pixel value of a first color component of a first color space;
generating, for the particular location in the frame of raw pixels, a vertical color difference signal and a horizontal color difference signal using information from the frame of raw pixels;
determining that the particular location is missing a color pixel value of a second color component of the first color space;
generating, for the particular location in the frame of raw pixels, a reconstructed color pixel value of the second color component based on the vertical color difference signal and the horizontal color difference signal; and
transforming, for the particular location in the frame of raw pixels, the vertical color difference signal and the horizontal color difference signal of the particular location in the frame of raw pixels into chrominance pixel values in a second color space that is different from the first color space;
wherein transforming the vertical color difference signal and the horizontal color difference signal into the chrominance pixel values in the second color space comprises:
determining an average of the vertical color difference signal and the horizontal color difference signal; and
using the average of the vertical color difference signal and the horizontal color difference signal to determine the chrominance pixel values in the second color space.

14. The non-transitory computer-readable medium of claim 13, wherein for the particular location:
the captured color pixel value is a captured green pixel value;
the horizontal color difference signal is the captured green pixel value minus a horizontal estimated blue pixel value; and
the vertical color difference signal is the captured green pixel value minus a vertical estimated red pixel value.

15. The non-transitory computer-readable medium of claim 13, wherein the process further comprises:
transforming, for the particular location in the frame of raw pixels, the captured color pixel value of the first color component to a brightness pixel value in the second color space.

16. The non-transitory computer-readable medium of claim 15, wherein transforming the captured color pixel value of the first color component to the brightness pixel value in the second color space is performed without using a color pixel value of a second color component of the first color space.

17. The non-transitory computer-readable medium of claim 16, wherein transforming the captured color pixel value of the first color component to the brightness pixel value in the second color space is performed without using a color pixel value of a third color component of the first color space.

* * * * *